US012667624B2

(12) United States Patent
Kim et al.

(10) Patent No.: US 12,667,624 B2
(45) Date of Patent: Jun. 30, 2026

(54) GIP DERIVATIVE, LONG-ACTING CONJUGATE THEREOF, AND PHARMACEUTICAL COMPOSITION COMPRISING SAME

(71) Applicant: HANMI PHARM. CO., LTD., Hwaseong-si (KR)

(72) Inventors: Eun Jung Kim, Hwaseong-si (KR); Jae Hyuk Choi, Hwaseong-si (KR); Won Ki Kim, Hwaseong-si (KR); Nyeong Sang Yoo, Hwaseong-si (KR); Hyeon Joo Im, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 598 days.

(21) Appl. No.: 18/031,937

(22) PCT Filed: Oct. 18, 2021

(86) PCT No.: PCT/KR2021/014456
§ 371 (c)(1),
(2) Date: Apr. 14, 2023

(87) PCT Pub. No.: WO2022/080984
PCT Pub. Date: Apr. 21, 2022

(65) Prior Publication Data
US 2023/0381331 A1 Nov. 30, 2023

(30) Foreign Application Priority Data
Oct. 16, 2020 (KR) ......................... 10-2020-0134479

(51) Int. Cl.

| | |
|---|---|
| *A61K 47/68* | (2017.01) |
| *A61K 47/60* | (2017.01) |
| *A61P 29/00* | (2006.01) |
| *A61P 37/00* | (2006.01) |
| *C07K 14/575* | (2006.01) |

(52) U.S. Cl.
CPC .............. *A61K 47/68* (2017.08); *A61K 47/60* (2017.08); *A61P 29/00* (2018.01); *A61P 37/00* (2018.01); *C07K 14/575* (2013.01)

(58) Field of Classification Search
CPC ......... A61K 47/68; A61K 47/60; A61P 37/00; A61P 29/00; C07K 14/575
See application file for complete search history.

(56) References Cited

U.S. PATENT DOCUMENTS

| | | | |
|---|---|---|---|
| 2014/0018291 A1 * | 1/2014 | Vignati ................. | A61K 45/06 514/5.3 |
| 2016/0257729 A1 | 9/2016 | Just et al. | |
| 2022/0213164 A1 | 7/2022 | Oh et al. | |

FOREIGN PATENT DOCUMENTS

| | | |
|---|---|---|
| EP | 4 230 218 A1 | 8/2023 |
| JP | 2017-503474 A | 2/2017 |
| KR | 10-2019-0104958 A | 9/2019 |
| WO | 2012088116 A2 | 6/2012 |
| WO | 2018/152172 A1 | 8/2018 |
| WO | 2020/067575 A1 | 4/2020 |

OTHER PUBLICATIONS

Nearmeen M. Rashad et al., "Serum and expression profiles of glucose-dependent insulinotropic polypeptide in correlation with cardiometabolic risk factors among patients with systemic lupus erythematosus", The Egyptian Journal of Internal Medicine, 2019, pp. 754-762, vol. 31.
International Search Report of PCT/KR2021/014456 dated Jan. 24, 2022 [PCT/ISA/210].
Extended European Search Report issued Dec. 18, 2024 in Patent Application No. 21880630.5.

* cited by examiner

*Primary Examiner* — Li N Komatsu
(74) *Attorney, Agent, or Firm* — Sughrue Mion, PLLC

(57) ABSTRACT

Provided are a GIP derivative, a pharmaceutically acceptable salt or solvate thereof, or a long-acting conjugate thereof, or a pharmaceutical composition including the same for preventing or treating inflammatory or autoimmune disease.

22 Claims, 5 Drawing Sheets

Specification includes a Sequence Listing.

FIG.  1

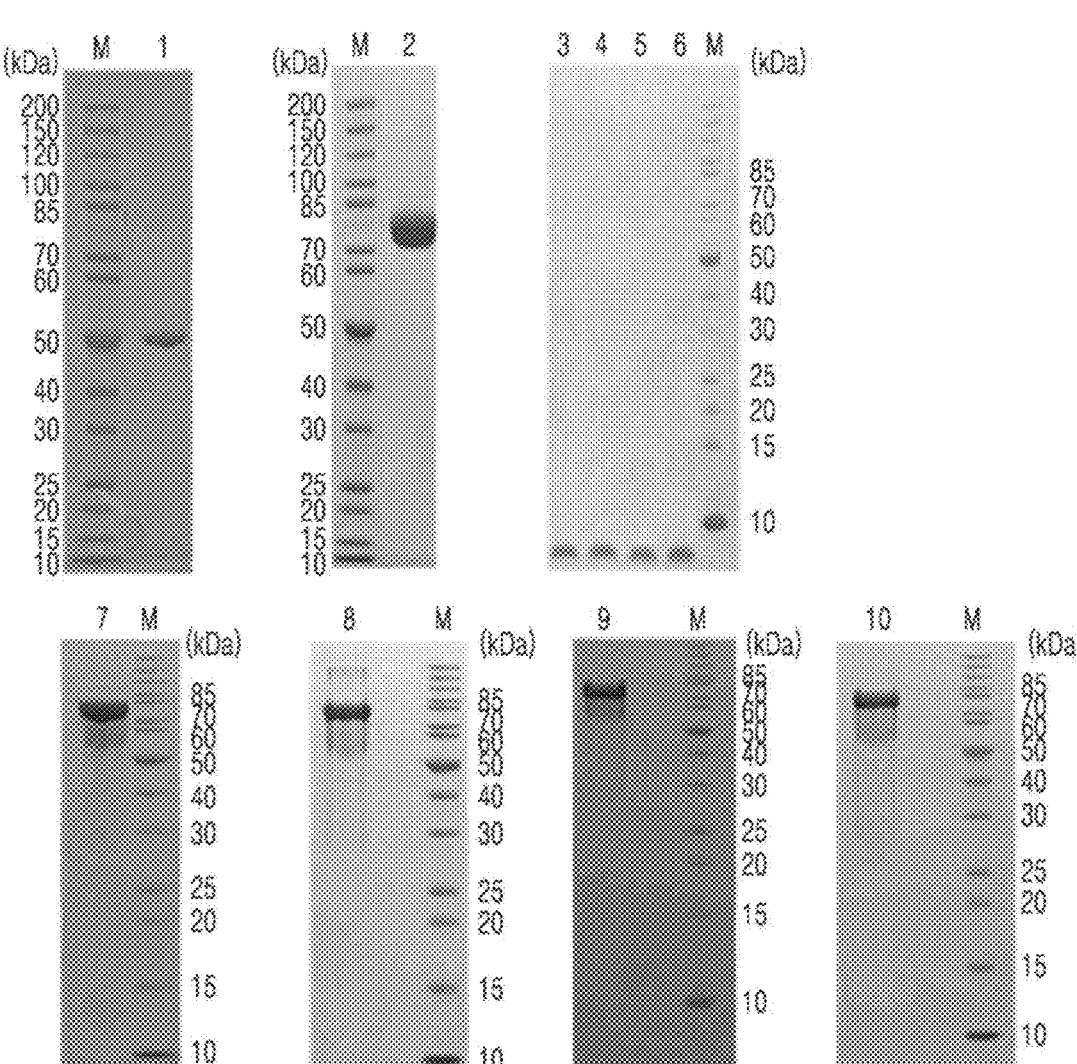

(NON-REDUCING CONDITION)

M: PROTEIN SIZE MARKER

1: IMMUNOGLUBULIN Fc
2: PEG-IMMUNOGLUBULIN Fc

3: GIP DERIVATIVE (SEQ ID NO: 11)
4: GIP DERIVATIVE (SEQ ID NO: 17)
5: GIP DERIVATIVE (SEQ ID NO: 21)
6: GIP DERIVATIVE (SEQ ID NO: 24)

7: LONG-ACTING GIP DERIVATIVE (SEQ ID NO: 11) CONJUGATE
8: LONG-ACTING GIP DERIVATIVE (SEQ ID NO: 17) CONJUGATE
9: LONG-ACTING GIP DERIVATIVE (SEQ ID NO: 21) CONJUGATE
10: LONG-ACTING GIP DERIVATIVE (SEQ ID NO: 24) CONJUGATE

FIG. 2

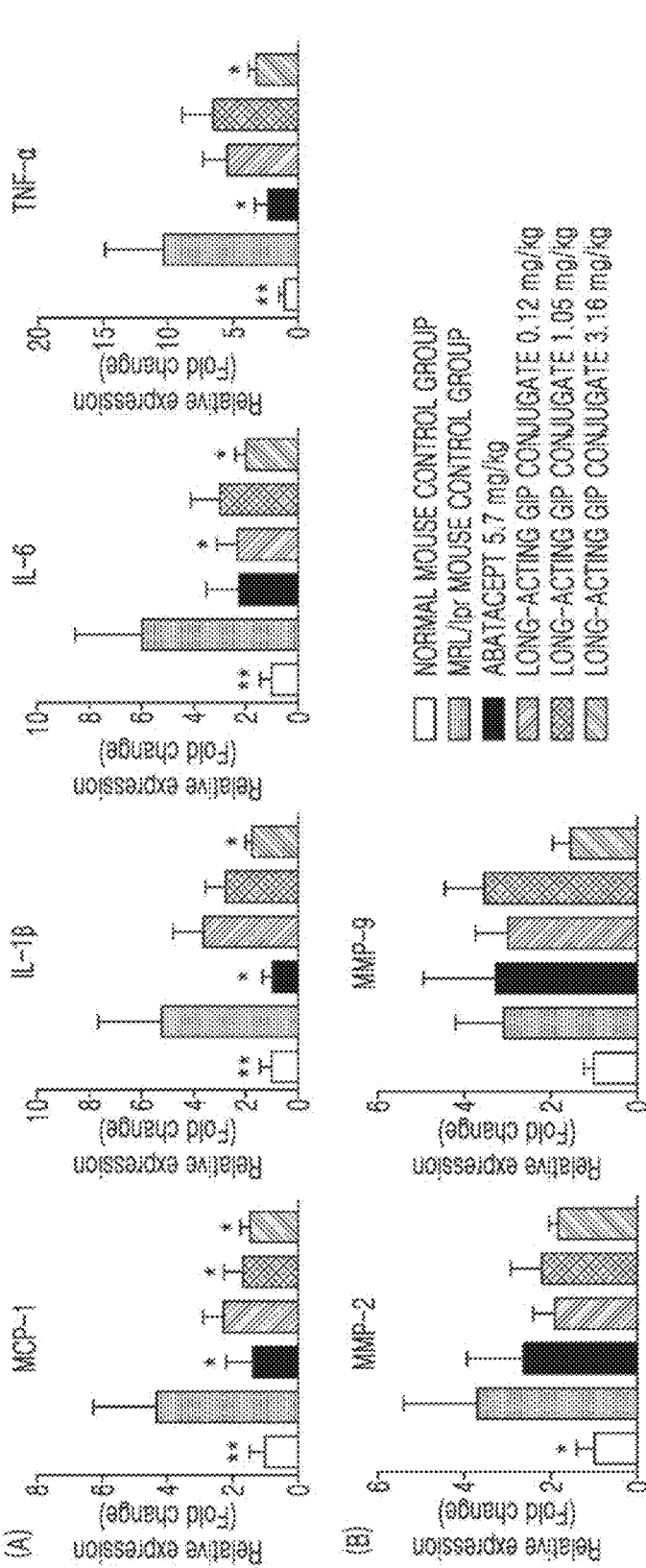
FIG. 4

GIP DERIVATIVE, LONG-ACTING CONJUGATE THEREOF, AND PHARMACEUTICAL COMPOSITION COMPRISING SAME

CROSS REFERENCE TO RELATED APPLICATIONS

This application is a National Stage of International Application No. PCT/KR2021/014456 filed on Oct. 18, 2021, claiming priority based on Korean Patent Application No. 10-2020-0134479 filed on Oct. 16, 2020.

INCORPORATION BY REFERENCE OF SEQUENCE LISTING

The content of the electronically submitted sequence listing, file name: Q286817SequenceListing01262026.txt; size: 31,009 bytes; and date of creation: Jan. 26, 2026, filed herewith, is incorporated herein by reference in its entirety.

TECHNICAL FIELD

The present disclosure relates to a GIP derivative, a long-acting conjugate thereof, a pharmaceutical composition comprising the same for prevention or treatment of inflammatory or autoimmune diseases.

BACKGROUND ART

Vasculitis is a disease caused by immune cells attacking blood vessels or blood vessel walls and inducing inflammation in the blood vessel walls. Vasculitis can be classified according to various classification methods, but currently the most used classification method is the classification according to the size of the invaded blood vessels as proposed by Jennette et al. (Jennette JC, Falk RJ, Andrassy K et al. Nomenclature of systemic vasculitides. Proposal of an international consensus conference. Arthritis Rheum 37:187-92, 1994).

Takayasu arteritis (TA) and giant cell arteritis (GCA) are representative large vessel vasculitis (LVV) affecting large vessels such as the aorta. Symptoms of vasculitis can result from direct damage to blood vessels or from indirect damage to tissues in which blood supply is disrupted or reduced. The symptoms vary depending on the size, location, and extent of damage to the blood vessels where inflammation is caused. Since vasculitis has various symptoms and is non-specific, it is difficult to diagnose early and is often diagnosed only after vascular deformation has progressed considerably, resulting in difficulties in treatment. In addition, since the cause of both TA and GCA is unknown and there are differences depending on race, region, and gender, it is a rare disease with a rare occurrence, and in this regard, active research has not been conducted.

The treatment of vasculitis mostly utilizes glucocorticoids to relieve inflammation, but due to the nature of steroids, side effects are great when used in high doses or for a long period of time. In addition, when the administration of glucocorticoids is stopped or the dose is reduced, problems such as recurrence of relieved symptoms occur.

LVV is one of the fields with high unmet demand because the development of fundamental treatment is still insufficient. Accordingly, development of an appropriate therapeutic agent is required to prevent progression of vasculitis to an irreversible vascular lesion with fewer side effects and to prevent complications that may occur in the future.

In the case of vasculitis and arteriosclerosis, these are common in that the tissue where a disease symptom appears is a blood vessel and that these are chronic inflammatory disease, but can be distinguished according to whether lipids are involved in the occurrence of the disease. Arteriosclerosis has a disease generation pathway in which lipids in the blood are accumulated on the walls of blood vessels and narrow the blood vessels, and vasculitis has a disease generation pathway in which blood vessels invading the walls of blood vessels cause an inflammatory reaction. Therefore, vasculitis and arteriosclerosis are different in pathophysiology as well as in the pathogenesis of the disease, and the treatment thereof is also different.

A glucose-dependent insulinotropic polypeptide (GIP) is a representative hormone (incretin hormone) among those secreted from the gastrointestinal tract, and is also a neuro-hormone secreted in response to food intake e. The GIP is a hormone consisting of 42 amino acids secreted from K cells in the small intestine, and is well known to help maintain homeostasis of blood glucose by promoting secretion of insulin or glucagon in the pancreas in a blood glucose concentration-dependent manner. Recent studies have reported diet suppression effects of the GIP.

Meanwhile, in the case of a native GIP, the activity thereof is lost when N-terminal is cleaved by an enzyme, dipeptidyl peptidase-4 (DPP-4), and this reaction occurs at a very high speed in the body. Thus, the half-life of the GIP in the human body is known to be very short, only about 7 minutes (J Clin Endocrinol Metab. 2000 October; 85(10):3575-81). Therefore, when utilizing efficacy of the GIP for the development of a therapeutic agent, it is required to develop a derivative having increased persistence in the body.

Accordingly, the inventors of the present disclosure developed a long-acting GIP derivative conjugate showing high activity in a human GIP receptor and having improved duration in the body, and by confirming the potential of the long-acting GIP derivative conjugate as a therapeutic agent for vasculitis, completed the present disclosure.

DISCLOSURE

Technical Problem

Provided is a novel GIP derivative.

Provided is a polynucleotide encoding the GIP derivative.

Provided is a vector including the polynucleotide.

Provided is a host cell including the polynucleotide or the vector.

Provided is a conjugate in which the GIP derivative is conjugated with a biocompatible material that increases the half-life in vivo.

Provided is a pharmaceutical composition for preventing or treating inflammatory or autoimmune disease, including the GIP derivative, a pharmaceutically acceptable salt or solvate thereof, or the conjugate.

Provided is a method of preventing or treating inflammatory or autoimmune disease, the method including administering the GIP derivative, the pharmaceutically acceptable salt or solvate thereof, the conjugate, or the pharmaceutical composition, in an effective amount to a subject in need thereof.

Provided is use of the GIP derivative, a pharmaceutically acceptable salt thereof, a solvate, or the conjugate for use in the preparation of a drug for preventing or treating the inflammatory or autoimmune disease.

Technical Solution

Throughout the present specification, not only the conventional 1-letter codes and 3-letter codes for amino acids present in nature, but also the 3-letter codes, such as α-aminoisobutyric acid (Aib) and the like, generally used for other amino acids, are used. In addition, the amino acids mentioned in abbreviation in the present specification are described according to the IUPAC-IUB nomenclature.

alanine Ala, A arginine Arg, R
asparagine Asn, N aspartic acid Asp, D
cysteine Cys, C glutamic acid Glu, E
glutamine Gln, Q glycine Gly, G
histidine His, H isoleucine Ile, I
leucine Leu, L lysine Lys, K
methionine Met, M phenylalanine Phe, F
proline Pro, P serine Ser, S
threonine Thr, T tryptophan Trp, W
tyrosine Tyr, Y valine Val, V An aspect of the disclosure provides a GIP derivative.

A "glucose-dependent insulinotropic polypeptide or a gastric inhibitory polypeptide (GIP)" is a hormone secreted from K cells in the small intestine when stimulated by food intake, and was first reported as a substance involved in regulating blood sugar concentration.

The "GIP derivative" may be a native GIP in which at least one amino acid in the native GIP sequence undergoes modification. The modification may be selected from the group consisting of substitution, addition, deletion, and modification, or a combination of two or more thereof. The amino acid sequence to be added may be derived from the native GIP amino acid sequence, but is not limited thereto.

The GIP derivative may be a peptide having activity on a GIP receptor. The "peptide having activity on the GIP receptor" refers to a peptide having a significant level of activity on the GIP receptor, and specifically, having in vitro activity on the GIP receptor of about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, about 100% or more, or about 100 to about 500%, or about 100% to about 200% compared to a native ligand (native GIP). A method of measuring the in vitro activity of the peptide having activity on the GIP receptor can be referred to Example 2 of the present specification, but is not particularly limited thereto. Any method known in the art may be appropriately used to measure the in vitro activity.

The term "about" refers to a range including all of ±0.5, ±0.4, ±0.3, ±0.2, ±0.1, etc., and includes all ranges equal to or similar to a numerical value following the term "about", but is not limited thereto.

In an embodiment, the GIP derivative may be one in which conservative substitution have occurred in 1, 2, 3, 4, 5, 6, 7, 8, 9, 10, or more amino acids in the native or unmutated GIP protein, but is not limited thereto.

The term "conservative substitution" refers to substitution of one amino acid with another amino acid having similar structural and/or chemical properties. The GIP derivative may have, for example, one or more conservative substitutions while still remaining the biological activity of the native or unmutated GIP protein. Such amino acid substitution may generally occur based on similarities in polarity, charge, solubility, hydrophobicity, hydrophilicity, and/or amphipathic nature. For example, a positively charged (basic) amino acid may include arginine, lysine, and histidine; a negatively charged (acidic) amino acid may include glutamic acid and aspartic acid; an aromatic amino acid may include phenylalanine, tryptophan, and tyrosine; and a hydrophobic amino acid may include alanine, valine, isoleucine, leucine, methionine, phenylalanine, tyrosine, and tryptophan. In addition, the amino acids may be classified into amino acids with electrically charged side chains and amino acids with uncharged side chains. Amino acids with electrically charged side chains may include aspartic acid, glutamic acid, lysine, arginine, and histidine, and amino acids with uncharged side chains may be further classified into nonpolar amino acids and polar amino acids. The nonpolar amino acid may include glycine, alanine, valine, leucine, isoleucine. methionine, proline, etc.; and the polar amino acid may include serine, threonine, cysteine, asparagine, glutamine, etc. The conservative substitution with amino acids having similar properties described above is expected to exhibit the same or similar activity of the amino acids.

The GIP derivative may be non-naturally occurring produced.

The GIP derivative may be an isolated peptide.

In an embodiment, the GIP derivative may be a peptide including the amino acid sequence represented by General Formula 1:

```
                                    (SEQ ID NO: 58)
Tyr-Aib(aminoisobutyric acid)-Glu-Gly-Thr- Phe-Ile-Ser-Asp-Tyr-Ser-Ile-Xaa13-Xaa14-

Xaa15-Xaa16-Xaa17-Ala-Xaa19-Xaa20-Xaa21-

Phe-Xaa23-Xaa24-Trp-Leu-Xaa27-Xaa28-Xaa29-

Xaa30-Xaa31-Xaa32-Xaa33-Xaa34-Xaa35-Xaa36-

Xaa37-Xaa38-Xaa39-Xaa40-Xaa41-Xaa42-Xaa43
(General Formula 1)
``` wherein, in General Formula 1,

Xaa13 may be alanine (Ala, A), Aib, tyrosine (Tyr, Y), or glutamine (Gln, Q),

Xaa14 may be methionine (Met, M) or leucine (Leu, L),

Xaa15 may be aspartic acid (Asp, D) or glutamic acid (Glu, E),

Xaa16 may be alanine (Ala, A), lysine (Lys, K), or glycine (Gly, G),

Xaa17 may be isoleucine (Ile, I) or glutamine (Gln, Q),

Xaa19 may be glutamine (Gln, Q) or alanine (Ala, A),

Xaa20 may be glutamine (Gln, Q), Aib, or lysine (Lys, K),

Xaa21 may be aspartic acid (Asp, D) or glutamic acid (Glu, E),

Xaa23 may be valine (Val, V) or isoleucine (Ile, I),

Xaa24 may be asparagine (Asn, N), alanine (Ala, A), or glutamine (Gln, Q),

Xaa27 may be leucine (Leu, L) or isoleucine (Ile, I),

Xaa28 may be alanine (Ala, A) or Aib,

Xaa29 may be glutamine (Gln, Q) or glycine (Gly, G),

Xaa30 may be lysine (Lys, K), glycine (Gly, G), or histidine (His, H),

Xaa31 may be proline (Pro, P), glycine (Gly, G), or cysteine (Cys, C),

Xaa32 may be serine (Ser, S) or lysine (Lys, K), or may be absent,

Xaa33 may be serine (Ser, S) or lysine (Lys, K), or may be absent,

Xaa34 may be glycine (Gly, G) or asparagine (Asn, N), or may be absent,

Xaa35 may be alanine (Ala, A) or aspartic acid (Asp, D), or may be absent,

Xaa36 may be proline (Pro, P) or tryptophan (Trp, W), or may be absent,

Xaa37 may be proline (Pro, P) or lysine (Lys, K), or may be absent,

Xaa38 may be proline (Pro, P) or histidine (His, H), or may be absent,

Xaa39 may be serine (Ser, S), asparagine (Asn, N), or cysteine (Cys, C), or may be absent, Xaa40 may be cysteine (Cys, C) or isoleucine (Ile, I), or may be absent, Xaa41 may be threonine (Thr, T) or may be absent, Xaa42 may be glutamine (Gln, Q) or may be absent, and Xaa43 may be cysteine (Cys, C) or may be absent.

Exemplary types of such a peptide may include any one amino acid sequence selected from the group consisting of SEQ ID NOs: 1 to 26.

In one or more embodiments, the peptide may include the amino acid sequence represented by General Formula 2:

(SEQ ID NO: 59)
Tyr-Aib(aminoisobutyric acid)-Glu-Gly-Thr-Phe-Ile-

Ser-Asp-Tyr-Ser-Ile-Xaa13-Xaa14-Xaa15-Xaa16-Xaa17-

Ala-Xaa19-Xaa20-Xaa21-Phe-Val-Xaa24-Trp-Leu-Xaa27-

Xaa28-Xaa29-Xaa30-Xaa31-Xaa32-Xaa33-Xaa34-Xaa35-

Xaa36-Xaa37-Xaa38-Xaa39-Xaa40-Xaa41-Xaa42-Xaa43

(General Formula 2)

wherein, in General Formula 2,

Xaa13 may be alanine (Ala, A), Aib, or tyrosine (Tyr, Y),

Xaa14 may be methionine (Met, M) or leucine (Leu, L),

Xaa15 may be aspartic acid (Asp, D) or glutamic acid (Glu, E),

Xaa16 may be alanine (Ala, A) or lysine (Lys, K),

Xaa17 may be isoleucine (Ile, I) or glutamine (Gln, Q),

Xaa19 may be glutamine (Gln, Q) or alanine (Ala, A),

Xaa20 may be glutamine (Gln, Q), Aib, or lysine (Lys, K),

Xaa21 may be aspartic acid (Asp, D) or glutamic acid (Glu, E),

Xaa24 may be asparagine (Asn, N) or glutamine (Gln, Q),

Xaa27 may be leucine (Leu, L) or isoleucine (Ile, I),

Xaa28 may be alanine (Ala, A) or Aib,

Xaa29 may be glutamine (Gln, Q) or glycine (Gly, G),

Xaa30 may be lysine (Lys, K), glycine (Gly, G), or histidine (His, H),

Xaa31 may be proline (Pro, P) or glycine (Gly, G),

Xaa32 may be serine (Ser, S) or lysine (Lys, K),

Xaa33 may be serine (Ser, S) or lysine (Lys, K),

Xaa34 may be glycine (Gly, G) or asparagine (Asn, N),

Xaa35 may be alanine (Ala, A) or aspartic acid (Asp, D),

Xaa36 may be proline (Pro, P) or tryptophan (Trp, W),

Xaa37 may be proline (Pro, P) or lysine (Lys, K),

Xaa38 may be proline (Pro, P) or histidine (His, H),

Xaa39 may be serine (Ser, S), asparagine (Asn, N), or cysteine (Cys, C),

Xaa40 may be cysteine (Cys, C) or isoleucine (Ile, I), or may be absent,

Xaa41 may be threonine (Thr, T) or may be absent,

Xaa42 may be glutamine (Gln, Q) or may be absent, and

Xaa43 may be cysteine (Cys, C) or may be absent.

Exemplary types of such a peptide may include any one amino acid sequence selected from the group consisting of SEQ ID NOs: 11, 17, and 19 to 26.

In one or more embodiments, the peptide may include the amino acid sequence represented by General Formula 3:

(SEQ ID NO: 60)
Tyr-Aib(aminoisobutyric acid)-Glu-Gly-Thr-Phe-Ile-

Ser-Asp-Tyr-Ser-Ile-Xaa13-Xaa14-Xaa15-Xaa16-Xaa17-

Ala-Xaa19-Xaa20-Xaa21-Phe-Val-Asn-Trp-Leu-Leu-

Xaa28-Xaa29-Xaa30-Xaa31-Xaa32-Xaa33-Xaa34-Xaa35-

Xaa36-Xaa37-Xaa38-Xaa39-Xaa40-Xaa41-Xaa42-Xaa43

(General Formula 3)

wherein, in General Formula 3,

Xaa13 may be alanine (Ala, A) or Aib,

Xaa14 may be methionine (Met, M) or leucine (Leu, L),

Xaa15 may be aspartic acid (Asp, D) or glutamic acid (Glu, E),

Xaa16 may be alanine (Ala, A) or lysine (Lys, K),

Xaa17 may be isoleucine (Ile, I) or glutamine (Gln, Q),

Xaa19 may be glutamine (Gln, Q) or alanine (Ala, A),

Xaa20 may be glutamine (Gln, Q) or Aib,

Xaa21 may be aspartic acid (Asp, D) or glutamic acid (Glu, E),

Xaa28 may be alanine (Ala, A) or Aib,

Xaa29 may be glutamine (Gln, Q) or glycine (Gly, G),

Xaa30 may be lysine (Lys, K), glycine (Gly, G), or histidine (His, H),

Xaa31 may be proline (Pro, P) or glycine (Gly, G),

Xaa32 may be serine (Ser, S) or lysine (Lys, K),

Xaa33 may be serine (Ser, S) or lysine (Lys, K),

Xaa34 may be glycine (Gly, G) or asparagine (Asn, N),

Xaa35 may be alanine (Ala, A) or aspartic acid (Asp, D),

Xaa36 may be proline (Pro, P) or tryptophan (Trp, W),

Xaa37 may be proline (Pro, P) or lysine (Lys, K),

Xaa38 may be proline (Pro, P) or histidine (His, H),

Xaa39 may be serine (Ser, S) or asparagine (Asn, N),

Xaa40 may be cysteine (Cys, C) or isoleucine (lie, 1),

Xaa41 may be threonine (Thr, T) or may be absent,

Xaa42 may be glutamine (Gln, Q) or may be absent, and

Xaa43 may be cysteine (Cys, C) or may be absent.

Exemplary types of such a peptide may include any one amino acid sequence selected from the group consisting of SEQ ID NOs: 11, 17, 21, and 24.

In one or more embodiments, in General Formula 3 (SEQ ID NO: 60),

Xaa13 may be alanine (Ala, A) or Aib,

Xaa14 may be leucine (Leu, L),

Xaa15 may be aspartic acid (Asp, D) or glutamic acid (Glu, E),

Xaa16 may be lysine (Lys, K),

Xaa17 may be glutamine (Gln, Q),

Xaa19 may be glutamine (Gln, Q) or alanine (Ala, A),

Xaa20 may be glutamine (Gln, Q) or Aib,

Xaa21 may be aspartic acid (Asp, D) or glutamic acid (Glu, E),

Xaa28 may be alanine (Ala, A) or Aib,

Xaa29 may be glutamine (Gln, Q),

Xaa30 may be glycine (Gly, G) or histidine (His, H),

Xaa31 may be proline (Pro, P),

Xaa32 may be serine (Ser, S),

Xaa33 may be serine (Ser, S),

Xaa34 may be glycine (Gly, G),

Xaa35 may be alanine (Ala, A),

Xaa36 may be proline (Pro, P),

Xaa37 may be proline (Pro, P),

Xaa38 may be proline (Pro, P),

Xaa39 may be serine (Ser, S),

Xaa40 may be cysteine (Cys, C), and

Xaa41 to Xaa43 may be absent.

Exemplary types of such a peptide may include any one amino acid sequence 15 selected from the group consisting of SEQ ID NOs: 17, 21, and 24.

In one or more embodiments, in General Formula 1,

Xaa13 may be alanine (Ala, A),

Xaa14 may be methionine (Met, M),

Xaa15 may be aspartic acid (Asp, D),

Xaa16 may be alanine (Ala, A),

Xaa17 may be isoleucine (Ile, I),

Xaa19 may be glutamine (Gln, Q),

Xaa20 may be glutamine (Gln, Q),

Xaa21 may be aspartic acid (Asp, D),

Xaa23 may be valine (Val, V),

Xaa24 may be asparagine (Asn, N),

Xaa27 may be leucine (Leu, L),

Xaa28 may be alanine (Ala, A),

Xaa29 may be glutamine (Gln, Q),

Xaa30 may be lysine (Lys, K),

Xaa31 may be glycine (Gly, G),

Xaa32 may be lysine (Lys, K),

Xaa33 may be lysine (Lys, K),

Xaa34 may be asparagine (Asn, N),

Xaa35 may be aspartic acid (Asp, D),

Xaa36 may be tryptophan (Trp, W),

Xaa37 may be lysine (Lys, K),

Xaa38 may be histidine (His, H),

Xaa39 may be asparagine (Asn, N),

Xaa40 may be isoleucine (Ile, I),

Xaa41 may be threonine (Thr, T),

Xaa42 may be glutamine (Gln, Q), and

Xaa43 may be cysteine (Cys, C).

However, in General Formulae 1 to 3, when the amino acid of any one of Xaa32 to Xaa43 is absent, subsequent amino acid sequences may also be present. In an embodiment, when Xaa32 is absent, Xaa33 to Xaa43 may be absent. In one or more embodiments, when Xaa41 is absent, Xaa42 to Xaa43 may be absent.

In one or more embodiments, the peptide may include any one amino acid sequence selected from the group consisting of SEQ ID NOs: 1 to 26. In addition, the peptide may consist essentially of any one amino acid sequence selected from the group consisting of SEQ ID NOs: 1 to 26, or may consist of any one amino acid sequence selected from the group consisting of SEQ ID NOs: 1 to 26.

In one or more embodiments, the peptide may include any one amino acid sequence selected from the group consisting of SEQ ID NOs: 11, 17, and 19 to 26. In addition, the peptide may consist essentially of any one amino acid sequence selected from the group consisting of SEQ ID NOs: 11, 17, and 19 to 26, or may consist of any one amino acid sequence selected from the group consisting of SEQ ID NOs: 11, 17, and 19 to 26.

In one or more embodiments, the peptide may include any one amino acid sequence selected from the group consisting of SEQ ID NOs: 11, 17, 21, and 24. In addition, the peptide may consist essentially of any one amino acid sequence selected from the group consisting of SEQ ID NOs: 11, 17, 21, and 24, or may consist of any one amino acid sequence selected from the group consisting of SEQ ID NOs: 11, 17, 21, and 24.

In one or more embodiments, the peptide may include any one amino acid sequence selected from the group consisting of SEQ ID NOs: 17, 21, and 24. In addition, the peptide may consist essentially of any one amino acid sequence selected from the group consisting of SEQ ID NOs: 17, 21, and 24, or may consist of any one amino acid sequence selected from the group consisting of SEQ ID NOs: 17, 21, and 24.

Although described as 'a peptide consisting of a particular SEQ ID NO' herein, such expression does not exclude a mutation that can occur by a meaningless sequence addition upstream or downstream of the amino acid sequence of the corresponding SEQ ID NO, or a silent mutation therein, as long as the peptide having such mutation has activity the same as or corresponding to that of the peptide which consists of the amino acid sequence of the corresponding SEQ ID NO. Even when the sequence addition or a mutation is present, it obviously belongs to the scope of the present disclosure. That is, even there are differences in some sequences of the peptide, the peptide belongs to the scope of the present disclosure as long as the sequence identity of at least a certain level is shown and the activity on the GIP receptor is exhibited. In detail, the peptide may include the amino acid sequence having a sequence identity of 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% or more with the amino acid sequences of SEQ ID NOs: 1 to 26, but is not limited thereto.

The term "homology" or "identity" as used herein refers to relatedness between two amino acid sequences or base sequences given, and is expressed as a percentage. Whether any two peptide sequences have homology, similarity, or identity may be determined by using known computer algorithms, such as the "FASTA" program using, for example, the default parameters as in Pearson et al. (1988) [Proc. Natl. Acad. Sci. USA 85]: 2444. Alternatively, the Needleman-Wunsch algorithm (Needleman and Wunsch, 1970, J. Mol. Biol. 48: 443-453), as performed in the Needleman program of the EMBOSS package (EMBOSS: The European Molecular Biology Open Software Suite, Rice et al., 2000, Trends Genet. 16: 276-277) (5.0.0 version. or later) may be used for the determination (other programs include the GCG program package (Devereux, J., et al, Nucleic Acids Research 12: 387 (1984)), BLASTP, BLASTN, FASTA (Atschul, [S.][F.,][ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, the BLAST of the National Center for Biotechnology Information database or ClustalW may be used to determine homology, similarity, or identity.

The homology, similarity, or identity of peptides may be, for example, determined by comparing sequence information using a GAP computer program, such as Needleman et al. (1970), J Mol Biol. 48: 443, as described in Smith and Waterman (Adv. Appl. Math (1981) 2:482). Briefly, the GAP program defines homology, similarity, or identity as the number of aligned symbols (i.e., amino acids), which are similar, divided by the total number of symbols in the shorter of the two sequences. Default parameters for the GAP program may include: (1) a unary comparison matrix (containing a value of 2 for identities and 0 for non-identities) and the weighted comparison matrix of Gribskov et al (1986) Nucl. Acids Res. 14: 6745, as described by Schwartz and Dayhoff, eds., Atlas Of Protein Sequence And Structure, National Biomedical Research Foundation, pp. 353-358 (1979) (or EDNAFULL substitution matrix (EMBOSS version of NCBI NUC4.4); (2) a penalty of 3.0 for each gap and an additional 0.10 penalty for each symbol in each gap (or a gap opening penalty of 10 and a gap extension penalty of 0.5); and (3) no penalty for end caps. Therefore, the term "homology" or "identity" used herein refers to relevance among sequences.

In an embodiment, the peptide including the amino acid sequence of General Formula 1 according to an aspect may be prepared by combining several methods for the preparation of various peptides.

The peptide according to an aspect may be synthesized by, depending on a length of the peptide, a method well known in the art, e.g., an automatic peptide synthesizer, and may be produced by genetic engineering technology. In detail, the peptide may be prepared by a standard synthesis method, a recombinant expression system, or any other method known in the art. Accordingly, the peptide according to an aspect may be prepared by various methods including, for example, the methods described below, but the methods are not limited thereto:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining the peptide by linking the peptide fragments, and then recovering the peptide.

In addition, the preparation of the peptide may include all of the modifications using L-type or D-type amino acids, and/or non-native type amino acids; and/or a modification of native sequence, for example, modification of a functional group on a side chain, an intramolecular covalent bonding, e.g., a ring formation between side chains, methylation, acylation, ubiquitination, phosphorylation, aminohexanation, biotinylation, etc. In addition, the modification may include substitutions into non-native compounds.

For the amino acids to be substituted or added during the modification, not only the 20 amino acids commonly found in human proteins, but also atypical or non-naturally occurring amino acids may be used. Commercial sources of atypical amino acids may include Sigma-Aldrich, ChemPep, and Genzyme pharmaceuticals, but are not limited thereto. For example, Aib(aminoisobutyric acid) may be prepared by using Strecker amino acid synthesis starting from acetone, but the synthesis method is not limited thereto. The peptides including these atypical or non-naturally occurring amino acids and typical peptide sequences may be synthesized and purchased from commercial peptide synthesis company, e.g., American Peptide Company or Bachem in USA or Anygen in Korea, but embodiments are not limited thereto.

In addition, the peptide may have an unmodified N-terminus and/or C-terminus. However, a peptide modified in a way that the N-terminus and/or C-terminus or the like is chemically modified or protected with an organic group to protect from proteinases in vivo and to increase stability, or that an amino acid is added to the terminus of the peptide also belongs to the peptide according to the one aspect. When the C-terminus is not modified, the terminus of the peptide may have a free carboxyl group, but embodiments are not particularly limited thereto.

In particular, in the case of the chemically synthesized peptide, the N- and C-terminus thereof are charged, and thus the N-terminus and/or C-terminus may be modified to remove these charges. For example, the N-terminus may be acetylated and/or the C-terminus may be amidated, but embodiments are not particularly limited thereto.

In an embodiment, the C-terminus of the peptide may not be modified or may be amidated, but embodiments are not limited thereto.

The peptide may include all forms of the peptide itself, a salt thereof (e.g., a pharmaceutically acceptable salt of the peptide), or a solvate thereof.

Types of the salt are not particularly limited. However, a salt in a form that is safe and effective for a subject, e.g., a mammal, is preferable, embodiments are not particularly limited thereto.

In addition, the peptide may be in any form that is pharmaceutically acceptable.

The term "pharmaceutically acceptable" as used herein refers to an amount sufficient to exhibit a therapeutic effect and not causing a side effect, and such an amount may easily be determined by one of ordinary skill in the art depending on factors well known in medical fields, such as a type of disease, age, weight health, and gender of a patient, sensitivity of a patient to drug, a route of administration, a method of administration, the number of administration, a treatment period, a combination of drugs, or drugs used simultaneously.

In an embodiment, the peptide may be in the form of a pharmaceutically acceptable salt thereof. The salt may include conventional acid addition salts used in the pharmaceutical field, such as in the field of inflammatory or autoimmune diseases. Examples of the acid addition salt are: a salt derived from inorganic acid such as hydrochloric acid, bromic acid, sulfuric acid, sulfamic acid, phosphoric acid, or nitric acid; and a salt derived from an organic acid such as acetic acid, propionic acid, succinic acid, glycolic acid, stearic acid, citric acid, maleic acid, malonic acid, methane sulfonic acid, tartaric acid, maleic acid, phenylacetic acid, glutamic acid, benzoic acid, salicylic acid, 2-acetoxybenzoic acid, fumaric acid, toluene sulfonic acid, oxalic acid, or trifluoroacetic acid. In addition, the salt may be a base addition salt such as ammonium, dimethylamine, monomethylamine, monoethylamine, and diethylamine. In addition, the salt may include a common metal salt form, for example, a salt derived from metal such as lithium, sodium, potassium, magnesium, or calcium. The acid addition salt, the base addition salt, or the metal salt may be prepared according to a conventional method. A pharmaceutically acceptable salt and a general methodology for preparing the same are well known in the art. For example, the document [P. Stahl, et al. Handbook of Pharmaceutical Salts: Properties, Selection and Use, 2nd Revised Edition (Wiley-VCH, 2011)]; [S. M. Berge, et al., "Pharmaceutical Salts," Journal of Pharmaceutical Sciences, Vol. 66, No. 1, January 1977] may be referred.

For condensation of the protected amino acid or peptide, various activating reagents useful in peptide synthesis, particularly preferably, a trisphosphonium salt, a tetramethyluronium salt, carbodiimide, and the like may be used. Examples of the trisphosphonium salt are benzotriazole-1-yl-oxy-tris(pyrrolidino)phosphonium hexafluorophosphate (PyBOP), brom-otris(pyrrolidino)phosphonium hexafluorophosphate (PyBroP), 7-azabenzotriazole-1-yl-oxy-tris(pyrrolidino)phosphonium hexafluorophosphate(PyAOP), examples of the tetramethyluronium salt are 2-(1H-benzotriazol-1-yl)-1,1,3,3-tetramethyluronium hexafluorophosphate (HBTU), 2-(7-azabenzotriazol-1-yl)-1,1,3,3-tetramethyluronium hexafluorophosphate(HATU), 2-(1H- benzotriazol-1-yl)-1,1,3,3-tetramethyluronium tetrafluoroborate (TBTU), 2-(5-norborene-2,3-dicarboxyimide)-1,1,3,3-tetramethyluronium tetrafluoroborate (TNTU), and O—(N-succinimidyl)-1,1,3,3-tetramethyluronium tetrafluoroborate (TSTU), and examples of the carbodiimide are N,N'-dicyclohexylcarbodiimide (DCC), N,N'-diisopropylcarbodiimide (DIPCDI), N-ethyl-N'-(3-dimethylaminopropyl)carbodiimide hydrochloric acid (EDCI-HCl), and the like. For condensation using these salts, addition of racemizing inhibitors [e.g., N-hydroxy-5-norbornene-2,3-dicarboxylic acid imide(HONB), 1-hydroxybenzotriazole (HOBt), 1-hydroxy-7-azabenzotriazole (HOAt), 3,4-dihydro-3-hydroxy-4-oxo-1,2,3-benzotriazine (HOOBt), ethyl 2-cyano-2-(hydroxyimido)acetate (Oxyma), etc] may be preferable. A solvent used for the condensation may be appropriately selected from those known to be useful for peptide condensation reactions. For example, amide such as anhydrous or water-containing N,N-dimethyl formamide, N,N-dimethylacetamide, N-methylpyrrolidone, etc., halogenated hydrocarbon such as methylene chloride, chloroform, etc., alcohol such as trifluoroethanol, phenol, etc., sulfoxide such as dimethylsulfoxide, tertiary amine such as pyridine, etc., ether dioxane, tetrahydrofuran, etc., nitrile such as acetonitrile, propionitrile, etc., ester such as methyl acetate, ethyl acetate, etc., an appropriate mixture thereof, and the like may be used. A temperature for reactions may be appropriately selected from the range known to be available for the peptide binding reaction, and may be generally selected from the range of about −20° C. to about 90° C. Activated amino acid derivatives may be generally used in excess of 1.5- to 6-fold. In the solid-phase synthesis, when a test using a ninhydrin reaction indicates that the condensation is insufficient, sufficient condensation can be performed by repeating the condensation reaction without removing the protecting group. When the condensation is still insufficient even after repeating the reaction, unreacted amino acid may be acetylated with an acid anhydride, acetylimidazole, etc., so that the influence on subsequent reactions can be avoided.

Examples of a protecting group for amino group of starting amino acid include benzyloxycarbonyl (Z), tert-butoxycarbonyl Boc), tert-pentyloxycarbonyl, isobonyloxycarbonyl, 4-methoxybenzyloxycarbonyl, 2-chlorobenzyloxycarbonyl(Cl-Z), 2-bromobenzyloxycarbonyl(Br-Z), adamantyloxycarbonyl, trifluoroacetyl, phthaloyl, formyl, 2-nitrophenylsulphenyl, diphenylphosphinothioyl, 9-fluorenylmethyloxycarbonyl (Fmoc), trityl, and the like.

Examples of carboxyl-protecting group for starting amino acid are, in addition to the $C_1$-$C_6$ alkyl group, the $C_3$-$C_{10}$ cycloalkyl group, and the $C_7$-$C_{14}$ aralkyl group described above, aryl, 2-adamantyl, 4-nitrobenzyl, 4-methoxybenzyl, 4-chlorobenzyl, fenacil, and benzyloxycarbonyl hydrazide, tert-butoxycarbonyl hydrazide, tritylhydrazide, and the like.

The hydroxyl groups of serine or threonine may be, for example, protected by esterification or etherification. Examples of groups suitable for esterification are a lower ($C_2$-$C_4$)alkynoyl group, such as an acetyl group, an aroyl group, such as a benzoyl group, and a group derived from an organic acid, and the like. In addition, examples of groups suitable for etherification are benzyl, tetrahydropyranyl, tert-butyl ($Bu^t$), trityl (Trt), and the like.

Examples of a protecting group for a phenolic hydroxyl group of thyrosine are Bzl, 2,6-dichlorobenzyl, 2-nitrobenzyl, Br-Z, tert-butyl, and the like.

Examples of a protecting group for imidazole of histidine are toluenesulfonyl (Tos), 4-methoxy-2,3,6-trimethylbenzenesulfonyl (Mtr), dinitrophenyl (DNP), benzyloxymethyl (Bom), tert-butoxymethyl (Bum), Boc, Trt, Fmoc, and the like.

Examples of a protecting group for a guanidino group of arginine are Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesithylene-2-sulfonyl (Mts), 2,2,4,6,7-pentamethyldihydrobenzofuran-5-sulfonyl (Pbf), Boc, Z, $NO_2$, and the like.

Examples of a protecting group for an amino group in side chains of lysine Z, CI-Z, trifluoroacetyl, Boc, Fmoc, Trt, Mtr, 4,4-dimethyl-2,6-dioxocyclohexylidenyl (Dde), and the like.

Examples of a protecting group for indolyl of tryptophan are formyl (For), Z, Boc, Mts, Mtr, and the like.

Examples of a protecting group for asparagine and glutamine are Trt, xantyl (Xan), 4,4'-dimethoxybenzhydryl (Mbh), 2,4,6-trimethoxybenzyl (Tmob), and the like.

Examples of an activated carboxyl group among the starting materials corresponding anhydride acid, an azide group, activity ester[ester with alcohol (e.g., pentachlorophenol, 2,4,5-trichlorophenol, 2,4-dinitrophenol, cyanomethylalcohol, paranitrophenol, HONB, N-hydroxysuccinimide, 1-hydroxybenzotriazole (HOBt), 1-hydroxy-7-azabenzotriazole (HOAt))], and the like. Examples of an activated amino group in the starting material are phosphorus amide and the like.

Examples of a method of removing the protecting group are: catalytic reduction in a hydrogen stream in the presence of a catalyst such as Pd-black or Pd-carbon; acid treatment with anhydrous fluorinated hydrogen, methanesulfonic acid, trifluoromethanesulfonic acid, trifluoroacetic acid (TFA), trimethylsilyl bromide (TMSBr), trimethylsilyl trifluoromethanesulfonate, tetrafluoroboronic acid, tris(trifluoro) boronic acid, boron triboromide, or a mixture solution thereof; base treatment using diisopropylethylamine, triethylamine, piperidine, piperazine, etc.; and reduction with sodium in liquid ammonia. The aforementioned removal reaction by acid treatment may be generally performed at a temperature in a range of −20° C. to 40° C., and the acid treatment may be efficiently performed by adding: anisole, phenol, thioanisole, metacresol, and paracresol; a cation scavenger, such as dimethylsulfide, 1,4-butanedithiol, 1,2-ethanedithiol, triisopropylsilane, etc. In addition, the 2,4-dinitrophenyl group used as the protecting group for histidine may be removed by thiophenol treatment; and the formyl group used as the protecting group for indole of tryptophan may be removed by deprotection not only by acid treatment in the presence of 1,2-ethanedithiol, 1,4-butanedithiol, and the like, but also by alkali treatment with dilute sodium hydroxide, dilute ammonia, and the like.

Protection of a functional group that should not be involved in the reaction between the starting material and the protecting group, removal of the protecting group, activation of a functional group involved in the reaction, and the like may be appropriately selected from known protecting groups and known methods.

For the peptide as used herein, the left end is the N-terminus (amino terminus) and the right end is the C-terminus (carboxyl terminus) according to conventional peptide markings. The C-terminus of the peptide may be any one of amide (—$CONH_2$), carboxyl group (—COOH), carboxylate (—COO—), alkylamide (—CONHR', wherein R' is alkyl), and ester (—COOR', wherein R' is alkyl or aryl).

In the method of preparing amide of the peptide, amide may be formed by solid-phase synthesis using a resin for amide synthesis, or by amidation of the α-carboxyl group of a carboxy-terminal amino acid. Then, the peptide chain is extended toward the amino group to a desired chain length, and afterwards, a peptide from which the protecting group for the N-terminal α-amino group of the peptide chain is removed and a peptide from which only the protecting group for the C-terminal carboxyl group is removed from the peptide chain are prepared. These two peptides are then condensed in the mixed solvent described above. For details of the condensation reaction, the same description above can be applied the same. After the protected peptide obtained by the condensation is purified, all protecting groups may be removed by the method described above, so as to obtain a desired peptide. By purifying the peptide using various publicly known methods of purification and the major fraction and freeze-drying, desired amide of the peptide may be prepared.

In an embodiment, the peptide may be in the form of a solvate of the peptide. The term "solvate" as used herein refers that the peptide or a salt thereof form a complex with a solvent molecule.

Another aspect provides a polynucleotide encoding the GIP derivative.

The GIP derivative is the same as described above.

The polynucleotide may be an isolated polynucleotide.

The polynucleotide may include DNA and RNA that encode a target protein.

The polynucleotide may be modified. The modification may include addition, deletion, or non-conservative or conservative substitution of nucleotides.

The polynucleotide may consist of a nucleotide sequence having sequence identity of 80% or more, 85% or more, 90% or more, 95% or more, 96% or more, 97% or more, 98% or more, or 99% or more with the corresponding sequence.

Another aspect provides a vector including the polynucleotide.

The term "vector" refers to a means for expressing a gene of interest in a host cell. For example, the vector may include a viral vector, such as a plasmid vector, a cosmic vector, a bacteriophage vector, an adenovirus vector, a retrovirus vector, and an adeno-associated viral vector. For a vector to be used as the recombinant vector, plasmids frequently used in the art (e.g., pSC101, pGV1106, pACYC177, CoIE1, pKT230, pME290, pBR322, pUC8/9, pUC6, pBD9, pHC79, pIJ61, pLAFR1, pHV14, pGEX series, pET series, pUC19, p426GPD, etc.), phages (e.g., Agt4AB, λ-Charon, AAz1, M13, etc.), or viruses (e.g., CMV, SV40, etc.) may be manipulated for the preparation, but embodiments are not limited thereto. A plasmid is currently the most commonly used form of vector, and thus the terms "plasmid" and "vector" as used herein may be occasionally used interchangeably.

In the recombinant vector, a promoter encoding the GIP derivative may be operably linked to a promoter. The term "operably linked" refers to a functional connection between a promoter sequence, which initiates and mediates the transcription of the polynucleotide encoding a target peptide, and the polynucleotide sequence.

The recombinant vector may be typically constructed as a vector for cloning or expression. For the expression vector, a conventional vector used in the art to express a foreign protein in plants, animals, or microorganisms may be used. The recombinant vector may be constructed through various methods known in the art.

The recombinant vector may be constructed by using prokaryotic cells or eukaryotic cells as a host. For example, when a vector in use is an expression vector and a prokaryotic cell is used as a host, the vector generally include a strong promoter capable of progressing transcription (e.g., a plyλ promoter, a trip promoter, a lac promoter, a tac promoter, a T7 promoter, etc.), a ribosome-binding site, and a sequence regulating the termination of transcription/translation. When a eukaryotic cell is used as a host, replication origins included in the vector may include an f1 replication origin, an SV40 replication origin, a pMB1 replication origin, an adeno replication origin, an AAV replication origin, a CMV replication origin, a BBV replication origin, etc., but embodiments are not limited thereto. In addition, promoters derived from the genome of mammalian cells (e.g., metallothionine promoter) or promoters derived from mammalian viruses (e.g., an adenovirus late promoter, a vaccinia virus 7.5K promoter, an SV40 promoter, a cytomegalovirus (CMV) promoter, and an HSV tk promoter) may be used, which generally have a polyadenylation sequence as a transcription termination sequence.

Another aspect provides a host cell including the polynucleotide or the vector.

The host cell may be an isolated cell.

For use as a host cell capable of being transformed with the recombinant vector, a host having high efficiency of DNA introduction and high expression efficiency of introduced DNA may be generally used. For example, known eukaryotic and prokaryotic hosts belonging to *E. coli, Pseudomonas, Bacillus, Streptomyces,* fungi, and yeast; insect cells of *Spodoptera frugiperda*(SF 9) or the like; and animal cells such as CHO, COS 1, COS 7, BSC 1, BSC40, BMT 10, etc., may be used, embodiments are not particularly limited thereto.

The insertion of the polynucleotide or a recombinant vector including the same into a host cell may be performed by a method widely known in the art. As a delivery method, for example, a calcium chloride (CaCl$_2$)) method or an electroporation method may be used when a host cell is a prokaryotic cell, or a microinjection method, a calcium phosphate precipitation method, an electroporation method, a liposome-mediated transfection method, a gene bombardment method, etc., may be used when a host cell is a eukaryotic cell.

The polynucleotide may be introduced into a host cell in the form of an expression cassette, which is a gene construct including all the essential elements required for self-expression. The expression cassette may generally include a promoter operably linked to the polynucleotide, a transcription termination signal, a ribosome-binding site, and a translation termination signal. The expression cassette may be in the form of an expression vector that enables self-replication. In addition, the polynucleotide may be introduced into a host cell as it is, and then operably linked to a sequence essential for expression in the host cell, but embodiments of the present disclosure are not limited thereto.

Another aspect provides a conjugate in which the GIP derivative is conjugated with a biocompatible material that increases the half-life in vivo.

The GIP derivative is the same as described above.

The biocompatible material may be used interchangeably with a carrier.

The conjugate may be an isolated conjugate.

The conjugate may exhibit activity on GIP receptors equal to or greater than that of native GIP, and at the same time, may exhibit increased efficacy of duration compared to that of a native GIP or GIP derivative to which a carrier is not linked. Therefore, the conjugate may be a long-acting conjugate. The term "long-acting conjugate" as used herein refers to a conjugate which exhibits an enhanced efficacy of duration compared to that of a native GIP or GIP derivative to which a biocompatible material is not linked. Therefore, the conjugate may be referred to as "a long-acting GIP derivative conjugate" or "a long-acting GIP derivative," or "a long-acting GIP conjugate". Such a conjugate may include not only the aforementioned forms, but also a form encapsulated in biodegradable nanoparticles.

The conjugate may be a non-naturally occurring conjugate.

The biocompatible material be linked to the GIP derivative through a covalent chemical bond or a non-covalent chemical bond, and may be linked thereto via a linker (L) by the covalent chemical bond, the non-covalent chemical bond, or a combination thereof. One or more side chains of amino acids in the GIP derivative may be conjugated to the biocompatible material to increase in vivo solubility and/or in vivo half-life and/or to increase bioavailability. Such modifications may also reduce clearance of therapeutic proteins and peptides. The aforementioned biocompatible material may be water soluble (amphiphilic or hydrophilic) and/or non-toxic and/or pharmaceutically acceptable.

The biocompatible material may be selected from the group consisting of a high-molecular weight polymer, fatty acid, cholesterol, albumin and a fragment thereof, an albumin-binding material, a polymer of repeating units of specific amino acid sequences, an antibody, an antibody fragment, an FcRn-binding material, in vivo connective tissue, a nucleotide, fibronectin, transferrin, a saccharide, heparin, and elastin, but embodiments are not particularly limited thereto.

Examples of the high-molecular weight polymer are polyethylene glycol (PEG), polypropylene glycol, an ethylene glycol-propylene glycol copolymer, polyoxyethylated polyol, polyvinylalcohol, disaccharide, polyvinylethylether, a biodegradable polymer, a lipid polymer, chitin, hyaluronic acid, an oligonucleotide, and a combination thereof. The disaccharide may include dextran, but embodiments are not particularly limited thereto.

The PEG is a term including all types of an ethylene glycol homopolymer, a PEG copolymer, or a monomethyl-substituted PEG polymer (mPEG), but embodiments are not particularly limited thereto.

The fatty acid may have a binding affinity to albumin in vivo, but embodiments are not particularly limited thereto.

The biocompatible material may include poly-amino acids such as poly-lysine, poly-aspartic acid, and poly-glutamic acid, but embodiments are not limited thereto.

In the case of elastin, elastin may be human tropoelastin, which is a water-soluble precursor, and may be a polymer of some sequences or some repeating units of tropoelastin, including, for example, all types of elastin-like polypeptides, but embodiments are not particularly limited thereto.

In an embodiment, the biocompatible material may be an FcRn-binding material. In detail, the FcRn-binding material may be an immunoglobulin Fc region, and in one or more embodiments, may be an IgG Fc region, and in one or more embodiments, may be a non-glycosylated IgG4 Fc region, but embodiments are not particularly limited thereto.

The term "immunoglobulin Fc region" as used herein refers to a region including the heavy chain constant region 2 (CH2) and/or the heavy chain constant region 3 (CH3), excluding the heavy chain and light chain variable regions of an immunoglobulin. The immunoglobulin Fc region may be one constitution that establishes a moiety of the conjugate according to an aspect.

Such an immunoglobulin Fc region may include a hinge region in the heavy chain constant region, but embodiments are not limited thereto.

In an embodiment, the immunoglobulin Fc region may include a specific hinge sequence at the N-terminus.

The term "hinge sequence" as used herein refers to a site located in the heavy chain to form a dimer of immunoglobulin Fc fragments through an inter disulfide bond.

In an embodiment, the hinge sequence may be mutated to have only one cysteine residue by deletion a part of the hinge sequence having the following amino acid sequences, embodiments are not particularly limited thereto:

```
                                   (SEQ ID NO: 27)
Glu-Ser-Lys-Tyr-Gly-Pro-Pro-Cys-Pro-Ser-Cys-Pro.
```

The hinge sequence may include only one cysteine residue by deletion of the 8th or 11th cysteine residue of the hinge sequence of SEQ ID NO: 27. The hinge sequence according to an embodiment may consist of 3 to 12 amino acids including only one cysteine residue, but embodiments are not particularly limited thereto. In detail, the hinge sequence according to an embodiment may have the following sequence:

```
                                   (SEQ ID NO: 28)
   Glu-Ser-Lys-Tyr-Gly-Pro-Pro-Pro-Ser-Cys-Pro, (SEQ ID NO: 29)
   Glu-Ser-Lys-Tyr-Gly-Pro-Pro-Cys-Pro-Ser-Pro, (SEQ ID NO: 30)
   Glu-Ser-Lys-Tyr-Gly-Pro-Pro-Cys-Pro-Ser (SEQ ID NO: 31)
   Glu-Ser-Lys-Tyr-Gly-Pro-Pro-Cys-Pro-Pro, (SEQ ID NO: 32)
   Lys-Tyr-Gly-Pro-Pro-Cys-Pro-Ser, (SEQ ID NO: 33)
   Glu-Ser-Lys-Tyr-Gly-Pro-Pro-Cys, (SEQ ID NO: 34)
   Glu-Lys-Tyr-Gly-Pro-Pro-Cys, (SEQ ID NO: 35)
   Glu-Ser-Pro-Ser-Cys-Pro (SEQ ID NO: 36)
   Glu-Pro-Ser-Cys-Pro, (SEQ ID NO: 37)
   Pro-Ser-Cys-Pro, (SEQ ID NO: 38)
   Glu-Ser-Lys-Tyr-Gly-Pro-Pro-Ser-Cys-Pro, (SEQ ID NO: 39)
   Lys-Tyr-Gly-Pro-Pro-Pro-Ser-Cys-Pro, (SEQ ID NO: 40)
   Glu-Ser-Lys-Tyr-Gly-Pro-Ser-Cys-Pro, (SEQ ID NO: 41)
   Glu-Ser-Lys-Tyr-Gly-Pro-Pro-Cys, (SEQ ID NO: 42)
   Lys-Tyr-Gly-Pro-Pro-Cys-Pro (SEQ ID NO: 43)
   Glu-Ser-Lys-Pro-Ser-Cys-Pro,
```

17

-continued

```
                                        (SEQ ID NO: 44)
  Glu-Ser-Pro-Ser-Cys-Pro, (SEQ ID NO: 45)
  Glu-Pro-Ser-Cys, (SEQ ID NO: 46)
  Ser-Cys-Pro.
```

In more detail, the hinge sequence may include the amino acid sequence of SEQ ID NO: 37 (Pro-Ser-Cys-Pro) or SEQ ID NO: 46 (Ser-Cys-Pro), but embodiments are not particularly limited thereto.

The immunoglobulin Fc region according to an embodiment may be in a form in which two molecules of the immunoglobulin Fc chain form a dimer due to the presence of the hinge sequence. In addition, in the conjugate of Formula 1 according to an embodiment, one end of the linker may be linked to one chain of the immunoglobulin Fc region that is in a dimeric form, but embodiments are not limited thereto.

The term "N-terminus" as used herein refers to the amino terminus of a protein or polypeptide, and may include the most end of the amino terminus or 1, 2, 3, 4, 5, 6, 7, 8, 9, or 10 or more amino acids from the most end of the amino terminus. The immunoglobulin Fc fragment of the present disclosure may include a hinge sequence at the N-terminus, but embodiments are not particularly limited thereto.

In addition, the immunoglobulin Fc region may be an extended Fc region including a part or the entirety of the heavy chain constant region 1 (CH1) and/or the light chain constant region (CL1), excluding the heavy chain and light chain variable regions of the immunoglobulin, as long as the immunoglobulin Fc region has an effect substantially the same as or improved compared to the native type. In addition, the immunoglobulin Fc region may be a region in which a fairly long part of the amino acid sequence corresponding to CH2 and/or CH3 is removed.

For example, the immunoglobulin Fc region may be selected from the group consisting of: (a) a CH1 domain, a CH2 domain, a CH3 domain, and a CH4 domain; (b) a CH1 domain and a CH2 domain; (c) a CH1 domain and a CH3 domain; (d) a CH2 domain and a CH3 domain; (e) a combination between one or two or more domains among a CH1 domain, a CH2 domain, a CH3 domain, and a CH4 domain, and an immunoglobulin hinge region or a part of the hinge region; and (f) a dimer between each domain of the heavy chain constant region and the light chain constant region, but embodiments are not limited thereto.

The immunoglobulin Fc region may be in a dimeric form, and one molecule of the GIP derivative may be covalently linked to a single Fc region in a dimeric form. Here, the immunoglobulin Fc and the GIP derivative may be interlinked by a non-peptide polymer. In addition, two molecules of the GIP derivative may be possibly conjugated in a symmetrical manner to a single Fc region in a dimeric form. Here, the immunoglobulin Fc and the GIP derivative may be interlinked by a non-peptide linker. However, embodiments are not limited thereto.

In addition, the immunoglobulin Fc region may include not only a native amino acid sequence, but also a sequence derivative thereof. An amino acid sequence derivative refers to an amino acid sequence having a difference in at least one amino acid residue among the native amino acid sequence due to deletion, insertion, non-conservative or conservative substitution, or a combination thereof.

For example, in the case of IgG Fc, amino acid residues at positions 214 to 238, 297 to 299, 318 to 322, or 327 to 331, which are known to be in the binding, may be used as suitable sites for modification. In addition, other various types of derivatives may be available in a that a site where a disulfide bond can be formed is deleted, some amino acid residues at the N-terminus of native Fc are deleted, or a methionine residue is added at the N-terminus of native Fc. In addition, to remove effector functions, a complement-binding site, such as a C1q-binding site, may be deleted, and an antibody dependent cell mediated cytotoxicity (ADCC) site may be deleted. Techniques of preparing such sequence derivatives of the immunoglobulin Fc region are disclosed in International Patent Publication Nos. WO 97/34631 and WO 96/32478.

Amino acid exchanges in proteins and peptides, which do not entirely alter the activity of the molecules, are known in the art (H. Neurath, R. L. Hill, The Proteins, Academic Press, New York, 1979). The most commonly occurring exchanges are exchanges between amino acid residues, such as Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, phosphorylation, sulfation, acrylation, glycosylation, methylation, farnesylation, acetylation, amidation, and the like may be used for the modification.

The aforementioned Fc derivative shows the same biological activity on that of the Fc region, and may have improved structural stability against heat, pH, etc.

In addition, the Fc region may be obtained from native forms isolated in vivo from humans or animals such as cows, goats, pigs, mice, rabbits, hamsters, rats, guinea pigs, etc., or may be recombinants or derivatives thereof obtained from transformed animal cells or microorganisms. Here, the obtaining of the Fc region in a native form may be a method of isolating a whole immunoglobulin from a living human or animal body and treating the isolated immunoglobulin with a protease. When treated papain, the immunoglobulin may be cleaved into Fab and Fc, or when treated with pepsin, the immunoglobulin may be cleaved into pF'c and F(ab)₂. The Fc or pF'c may be isolated by using size-exclusion chromatography, etc. In a more specific embodiment, a human-derived Fc region may be a recombinant immunoglobulin Fc region obtained from a microorganism.

In addition, the immunoglobulin Fc region may have natural glycans, increased glycans compared to the natural type, or decreased glycans compared to the natural type, or may be in a deglycosylated form. For the increase, decrease, or removal of the glycans of the immunoglobulin Fc, conventional methods such as a chemical method, an enzymatic method, and a genetic engineering method using a microorganism may be used. Here, the immunoglobulin Fc region in which the glycans are removed from Fc may have a significantly decreased binding affinity to the complement (c1q), and reduced or removed antibody-dependency cytotoxicity or complement-dependency cytotoxicity, and thus unnecessary immune responses in vivo are not caused. In this regard, an immunoglobulin Fc region in a deglycosylated or aglycosylated form may be more suitable to meet the original purpose as a drug carrier.

The term "deglycosylation" as used herein refers to an Fc region from which sugars are removed by enzymes, and the term "aglycosylation" as used herein refers to an unglycosylated FC region produced in prokaryotes, more specifically, E. coli.

In addition, the immunoglobulin Fc region may be derived from IgG, IgA, IgD, IgE, IgM, or a combination or hybrid thereof. In a detailed embodiment, the immunoglobulin Fc region may be derived from IgG or IgM, which are among the most abundant proteins in human blood, and in a more detailed embodiment, the immunoglobulin Fc region may be derived from IgG which is known to enhance the half-lives of ligand-binding proteins. In a more detailed embodiment, the immunoglobulin Fc region may be an IgG4 Fc region, and in a most specific embodiment, the immunoglobulin Fc region may be an aglycosylated Fc region derived from human IgG4, but embodiments are not limited thereto.

The term "combination" as used herein refers that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The GIP derivative may be linked to a biocompatible material through a linker.

The linker may be a peptide linker or a non-peptide linker.

When the linker is a peptide linker, the linker may include at least one amino acid, for example, 1 amino acid to 1,000 amino acids, but embodiments are not particularly limited thereto. The peptide linker may include Gly, Asn, and Ser residues, and may also include neutral amino acids such as Thr and Ala. For the linkage between the biocompatible material and the GIP derivative, various known peptide linkers may be used. In addition, the number of copies "n" may be adjusted in consideration of linker optimization to achieve proper separation between functional moieties or to maintain essential inter-moiety interactions. Other soluble linkers are known in the art, and for example, a GS linker, in which not only a polar amino acid residue is added to improve water solubility, but also amino acid residues, such as T and A, are added to maintain flexibility may be used. Therefore, in an embodiment, the linker may be a flexible linker including G, S, and/or T residues. The linker may have a general formula selected from (GpSs)n and (SpGs)n, wherein, independently, p may be an integer of 1 to 10, s may be an integer of 0 to 10, the sum of p and S may be an integer of 20 or less, and n may be an integer of 1 to 20. In detail, the linker may have, for example, a general formula of (GGGGS)n (SEQ ID NO: 47), (SGGGG)n (SEQ ID NO: 48), (SRSSG)n (SEQ ID NO: 49), (SGSSC)n (SEQ ID NO: 50), (GKSSGSGSESKS)n (SEQ ID NO: 51), (RPPPPC)n (SEQ ID NO: 52), (SSPPPPC)n (SEQ ID NO: 53), (GST-SGSGKSSEGKG)n (SEQ ID NO: 54), (GST-SGSGKSSEGSGSTKG)n (SEQ ID NO: 55), (GST-SGSGKPGSGEGSTKG)n (SEQ ID NO: 56), or (EGKSSGSGSESKEF)n (SEQ ID NO: 57), wherein n may be an integer of 1 to 20 or an integer of 1 to 10.

The "non-peptide linker" may include a biocompatible polymer in which at least two repeating units are linked. These repeating units may be linked with each other by any covalent bond instead of a peptide linkage. The non-peptide linker may be one constitution that establishes a moiety of the conjugate.

The terms "non-peptide linker" and "non-peptide polymer" may be used interchangeably.

In an embodiment, in the conjugate, the biocompatible material and the GIP derivative may be covalently linked through a non-peptide linker which includes a reactive group that can be linked to the biocompatible material, such as the immunoglobulin Fc region, and the GIP derivative at both ends of the conjugate, respectively.

In detail, the non-peptide linker may be selected from the group consisting of a peptide, a fatty acid, a saccharide, a high-molecular weight polymer, a low-molecular compound, a nucleotide, and a combination thereof.

Although not particularly limited thereto, the non-peptide linker may be selected from the group consisting of PEG, polypropylene glycol, an ethylene glycol-propylene glycol copolymer, polyoxyethylated polyol, polyvinylalcohol, a polysaccharide, polyvinyl ethyl ether, a biodegradable polymer such as polylactic acid (PLA) and polylactic-glycolic acid (PLGA), a lipid polymer, chitins, hyaluronic acid, an oligonucleotide, and a combination thereof. The polysaccharide may be dextran, but embodiments are not limited thereto.

In a more specific embodiment, the non-peptide polymer may be polyethylene glycol, embodiments are not particularly limited thereto. Therefore, the linker may include an ethylene glycol repeating unit. In addition, derivatives that are already known in the art and derivatives that can be easily prepared at the level of technology in the art belong to the scope of the present disclosure.

For use as the non-peptide linker, any polymer having a resistance to in vivo proteases may be used without limitation. The formula weight of the non-peptide polymer may be in a range of 1 kDa to 1,000 kDa, for example, 1 kDa to 100 kDa, and for example, 1 kDa to 20 kDa, but embodiments are not particularly limited thereto. In addition, the non-peptide linker may include not only a single type of a polymer but also a combination of different types of polymers. In an embodiment, the formula weight of the ethylene glycol repeating unit may be in a range of 1 kDa to 100 kDa, and for example, 1 kDa to 20 kDa.

In an embodiment, both ends of the non-peptide linker may each be linked to the biocompatible material, e.g., an amine group or a thiol group of the immunoglobulin Fc region, and an amine group or a thiol group of the GIP derivative.

In an embodiment, the non-polymer may include a reactive group at both ends thereof, respectively, which can be linked to the biocompatible material (e.g., the immunoglobulin Fc region) and the GIP derivative, specifically, an reactive group that can be linked to an amine group that is located at the N-terminus or lysine or to a thiol group of cysteine of the GIP derivative or the biocompatible material (e.g., the immunoglobulin Fc region), but embodiments are not particularly limited thereto.

In addition, the reactive group of the non-peptide polymer, which can be linked to the biocompatible material, e.g., the immunoglobulin Fc region, and the GIP derivative may be selected from the group consisting of an aldehyde group, a maleimide group, and a succinimide derivative, embodiments are not particularly limited thereto. In the above, an example of the aldehyde group is a propionaldehyde group or a butylaldehyde, but embodiments are not particularly limited thereto. In the above, as the succinimide derivate, succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate may be used, but embodiments are not particularly limited thereto.

In addition, the final product produced through reductive alkylation via an aldehyde bond may be more stable than that linked by an amide bond. The aldehyde reactor selectively reacts with the N-terminus at a low pH, and may form a covalent bond with a lysine residue at high pH, e.g., pH 9.0.

In addition, the reactive groups at both ends of the non-peptide linker may be identical to or different from each other. For example, a maleimide group may be provided at one end and an aldehyde group, a propionaldehyde group, or a butyl aldehyde group may be provided at the other end. However, as long as the biocompatible material, specifically, the immunoglobulin Fc region and the GIP derivative, can be conjugated at each end of the non-peptide linker, embodiments are not particularly limited thereto. For example, the non-peptide linker may include, as the reactive group, a maleimide group as the reactive group at one end and an aldehyde group, a propionaldehyde group, a butylaldehyde group, etc. at the other end.

When PEG is used as the non-peptide polymer having a reactive hydroxy group at both ends, the hydroxy group may be activated to various reactive groups by known chemical reactions, or PEG having a commercially available modified reactive group may be used to prepare the long-acting conjugate.

In an embodiment, the non-peptide polymer may be one which can be linked to a cysteine residue of the GIP derivative, and more specifically, to a —SH group of cysteine, embodiments are not particularly limited thereto.

When maleimide-PEG-aldehyde is used, the maleimide group may be linked to the —SH group of the GIP derivative by a thioether and the aldehyde group may be linked to the biocompatible material, specifically, a —$NH_2$ group of the immunoglobulin Fc through reductive alkylation. However, embodiments are not limited thereto, and the above is merely an exemplary embodiment.

In addition, in the conjugate, the reactive group of the non-peptide polymer may be linked to —$NH_2$ located at the N-terminus of the immunoglobulin Fc region, but this embodiment is merely an exemplary embodiment.

Therefore, the conjugate according to an aspect may be represented by Formula 1:

$$X\text{-}L\text{-}F \qquad \text{Formula 1}$$

wherein, in the formula above, X is the GIP derivative,
L is a linker,
F is a biocompatible material that increases the half-life of X in vivo, and
represents a bond between X and L and a bond between L and F.

In Formula 1, the GIP derivative, the linker, and the biocompatible material are the same as described above.

In Formula 1, L may be La, wherein a is 0 or a natural number, and when a is 2 or more, each of L(s) may be independent of each other.

In detail, the linker may be PEG represented by Formula 2, but embodiments are not limited thereto:

Formula 2 wherein n may be 10 to 2400, n may be 10 to 480, or n may be 50 to 250, but embodiments are not particularly limited thereto.

In the long-acting conjugate, a PEG moiety may include not only a —$(CH_2CH_2O)n$- structure but also an oxygen atom between an linking element and the —$(CH_2CH_2O)n$-, but embodiments are not limited thereto.

The PEG is a term including all types of an ethylene glycol homopolymer, a PEG copolymer, or an mPEG, but embodiments are not particularly limited thereto.

In an embodiment, - may represent a covalent bond between X and L and a bond between L and F.

The conjugate is confirmed to reduce the expression levels of inflammation-related genes IL-1β, IL-6, IL-12, IFN-γ, and TNF-α both in vitro and in vivo, and thus may be utilized for use in the prevention or treatment of inflammatory or autoimmune diseases.

The GIP derivative or the conjugate thereof was confirmed to reduce the expression levels of inflammation-related genes in the THP-1 cell line, which is a monocyte/macrophage cell line. A macrophage is known to secrete cytokines and chemokines in the early stage of infection in vasculitis-infected tissue, induce the progress of inflammation by utilizing other immune cells, and form giant cells. In addition, the GIP derivative or the conjugate thereof was confirmed to reduce the expression levels of inflammation-related genes in the aorta of obese mice induced with a high-fat diet. In addition, the GIP derivative or the conjugate thereof was confirmed not only to reduce the expression levels of inflammation-related genes in a model having a vasculitis disease, but also to reduce the expression levels of vascular remodeling factors, MMP-2 and MMP-9, which play an important role in the progression of vasculitis. In addition, the GIP derivative or the conjugate thereof was confirmed to reduce the expression of inflammation-related genes (e.g., IL-6 and TNF-α) in mice infused with angiotensin II. Therefore, the GIP derivative or the conjugate thereof may be utilized for use in the prevention or treatment of vasculitis.

The GIP derivative or the conjugate thereof may exhibit an effect of preventing or treating vasculitis by any one of the following:
(i) by reducing or suppressing the expression of inflammation-related genes in macrophages (wherein the inflammation-related genes are at least one selected from IL-1β, IL-6, IL-12, IFN-γ, and TNF-α);
(i) by reducing or suppressing the expression of inflammation-related genes in blood vessels (wherein the inflammation-related genes are at least one selected from MCP-1, IL-1α, IL-1β, IL-6, IFN-γ, and TNF-α); and
(iii) by reducing or suppressing the expression of angiogenic factors in blood vessels (wherein the angiogenic factors are at least one selected from MMP-2 and MMP-9).

Another aspect provides a pharmaceutical composition for preventing or treating inflammatory or autoimmune disease, comprising the GIP derivative, a pharmaceutically acceptable salt or solvate thereof, or the conjugate.

The GIP derivative, the pharmaceutically acceptable salt or solvate thereof, or the conjugate are the same as described above.

The term "prevention" as used herein refers to all kinds of actions associated with the suppression or delay of the occurrence of inflammatory or autoimmune diseases by the administration of the composition.

The term "treatment" as used herein refers to all kinds of actions associated with the improvement or advantageous changes of inflammatory or autoimmune diseases by the administration of the composition.

The "inflammatory or autoimmune disease" refers to a disease resulting from inflammation, arising from inflammation, or inducing inflammation, or the presence of an autoimmune response (i.e., an autoantigen or an immune response thereto) in a subject. The autoimmune disease may include diseases resulting from the breakdown of self-tolerance, which allows the adoptive immune system to react against autoantigens and mediate a damage in cells and tissues. In detail, the inflammatory or autoimmune disease may include inflammatory or autoimmune disease in a specific area of the body, for example, blood vessels, oral cavity, mucous membranes, stomach, pancreases, skin, eyes, pharynx, tonsils, ears, bones, joints, cartilage, brain, spinal cord, nerves, bone marrow, bladder, liver, muscle, thyroid, bile duct, kidney, etc.; a systemic inflammatory or autoimmune disease; etc., but embodiments are not particularly limited thereto.

In an embodiment, the inflammatory or autoimmune disease may include any one selected from the group consisting of: vasculitis; rheumatoid arthritis; Sjogren's syndrome; neuromyelitis optica (NMO); idiopathic thrombocytopenic purpura (ITP); thrombotic thrombocytopenic purpura (TTP); autoimmune thrombocytopenia; psoriasis; IgA nephropathy; IgM polyneuropathies; myasthenia gravis; diabetes mellitus; Reynaud's syndrome; and glomerulonephritis, but embodiments are not particularly limited thereto.

In an embodiment, the inflammatory or autoimmune disease may be vasculitis. The vasculitis may be classified according to the size of the blood vessel involved. The vasculitis may be large-vessel vasculitis, medium-vessel vasculitis, or small-vessel vasculitis. The vasculitis may be classified into: vasculitis associated with the largest arteries including the aorta and major branches; vasculitis associated with the medium-sized arteries; vasculitis associated with the small and medium-sized arteries; vasculitis associated with the small arteries; or vasculitis associated with the arteries and veins of various sizes.

In an embodiment, the vasculitis may be selected from the group consisting as follows, but embodiments are not particularly limited thereto:
- (1) vasculitis associated with large arteries, including: giant cell arteritis (GCA); Takayasu's arteritis (TA); aortitis in Cogan's syndrome; aortitis in spondylarthropathies; isolated aortitis, and the like;
- (2) vasculitis associated with medium arteries, including: Kawasaki disease; polyarteritis nodosa (PAN), and the like;
- (3) vasculitis associated with small and medium arteries, including antineutrophil cytoplasmic antibodies (ANCA)-associated vasculitis; granulomatosis with polyangiitis (GPA, former name: Wegener's granulomatosis (WG)); microscopic polyangiitis (MPA); eosinophilic granulomatosis with polyangiitis (EGPA) (or Churg-Strauss syndrome); primary angiitis of the central nervous system, and the like; and
- (4) vasculitis associated with small arteries, including IgA vasculitis (or Henoch-Schonlein); vasculitis related to rheumatoid arthritis, systemic lupus erythematosus, and Sjogren's syndrome; cryoglobulinemic vasculitis; drug-induced vasculitis, and the like.

The pharmaceutical composition may further include a pharmaceutically acceptable carrier. The pharmaceutically acceptable carrier may include, for oral administration, a binder, a glidant, a disintegrant, an excipient, a solubilizer, a dispersant, a stabilizer, a suspending agent, a colorant, and a flavoring agent, and the like; for injections, a buffer, a preservative, an analgesic, a solubilizer, an isotonic agent, a stabilizer, and the like; and for topical administration, a base, an excipient, a lubricant, and a preservative, and the like.

In an embodiment, the pharmaceutical composition may further include a pharmaceutically acceptable excipient.

The formulation type of the pharmaceutical composition may be prepared variously by combining with the aforementioned pharmaceutically acceptable carrier. For example, for oral administration, the pharmaceutical composition may be formulated into tablets, troches, capsules, elixirs, suspensions, syrups, wafers, etc. For injections, the pharmaceutical composition may be formulated into a single dosage ampoule or a multiple dosage form. Additionally, the pharmaceutically composition may be formulated into solutions, suspensions, tablets, capsules, and sustained-release formulations.

Meanwhile, examples of suitable carriers, excipients, and diluents for the formulation may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil. In addition, the pharmaceutical composition may further include a filler, an anti-coagulant, a lubricant, a humectant, a flavoring agent, an emulsifier, a preservative, etc.

The pharmaceutical composition may further include one or more other agents for treating the inflammatory or autoimmune disease. In detail, the other agents may include an anti-inflammatory agent or an immunosuppressive agent, but embodiments are not particularly limited thereto. In more detail, the other agents may include a therapeutic agent for vasculitis, but embodiments are not particularly limited thereto.

The term "anti-inflammatory agent" as used herein refers to a compound for treating an inflammatory disease or a symptom related thereto. Non-limiting examples of the anti-inflammatory agents include: but not limited thereto, a non-steroidal anti-inflammatory drug (NSAID; e.g., aspirin, ibuprofnaproxen, methyl salicylate, diflunisal, indometacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroid (e.g., prednisone, betamethasone, budesonide, cortisone, dexamethasone, hydrocortisone, methyl prednisolone, prednisolone, triamcinolone, and fluticasone), rapamycin (e.g., see document [Migita et al., Clin. Exp. Immunol. (1997) 108:199-203]; [Migita et al., Clin. Exp. Immunol. (1996) 104:86-91]; [Foroncewicz et al., Transpl. Int. (2005) 18:366-368]), a compound increasing levels of high-density lipoprotein (HDL) and HDL-cholesterol (e.g., see documents [Birjmohun et al. (2007) Arterioscler. Thromb. Vasc. Biol., 27:1153-1158]; [Nieland et al. (2007) J. Lipid Res., 48:1832-1845]; [Bloedon et al. (2008) J. Lipid Res., Samaha et al. (2006) Arterioscler. Thromb. Vasc. Biol., 26:1413-1414] disclosing use of rosiglitazone as an anti-inflammatory agent; and [Duffy et al. (2005) Curr. Opin. Cardiol., 20:301-306]), a rho-kinase inhibitor (e.g., see document [Hu, E. (2006) Rec. Patents Cardiovasc. Drug Discov., 1:249-263]), an antimalarial drug (e.g., hydroxychloroquine and chloroquine), acetaminophen, glucocorticoid, steroid, beta-agonist, anticholinergic, methyl xanthine, gold injection (e.g., sodium aurothiomalate), sulfasalazine, penicillamine, antiangiogenic drug, dapsone, psoralen, antiviral drug, statin (e.g., see document [Paraskevas et al. (2007) Curr. Pharm. Des., 13:3622-36]; [Paraskevas, K. I. (2008) Clin. Rheumatol. 27:281-287]), and an antibiotic (e.g., tetracycline). In a specific embodiment, the anti-inflammatory agent may be statin or a compound increasing levels of HDL and HDL-cholesterol.

The "immunosuppressant" and "immunosuppressive agent" as used herein may include compounds or compositions that cuppress the immune response or symptoms related thereto. Non-limiting examples of the immunosuppressant are a purin analogue (e.g., azathioprine), methotrexate, cyclosporine (e.g., cyclosporine A), cyclophosphamide, leflunomide, mycophenolate (mycophenolate mofetil), steroid (e.g., glucocorticoid and corticosteroid), methylprednisone, prednisone, a non-steroidal anti-inflammatory drug (NSAID), chloroquine, hydroxychloroquine, chlorambucil, a CD20 antagonist (e.g., rituximab, ocrelizumab, beltuzumab, or ofatumumab), abatacept, a TNF antagonist (e.g., infliximab, adalimumab, and etanercept), macrolide (e.g., pimecrolimus, tacrolimus (FK506), and sirolimus), dehydroepiandrosterone, lenalidomide, a CD40 antagonist (e.g., 25 an anti-CD40L antibody), abetimus sodium, a BLys antagonist (e.g., anti-BLyS (e.g., belimumab)), dactinomycin, bucillamine, penicillamine, leflunomide, mercaptopurine, a pyrimidine analogue (e.g., cytosine arabinoside), mizoribine, an alkylating agent (e.g., nitrogen mustard, phenylalanine mustard, busulfan, and cyclophosphamide), a folic acid antagonist (e.g., aminopterin and methotrexate), an antibiotic (e.g., rapamycin, actinomycin D, mitomycin C, puramycin, and chloramphenicol), human IgG, anti-lymphocyte globulin (ALG), an antibody (e.g., anti-CD3(OKT3), anti-CD4(OKT4), anti-CD5, anti-CD7, an anti-IL-2 receptor (e.g., daclizumab and basiliximab), anti-alpha/beta TCR, anti-ICAM-1, murononab-CD3, anti-IL-12, alemtuzumab, and an antibody to an immunotoxin), 1-methyltryptophan, and a derivative and analogue thereof. In a specific embodiment, the immunosuppressant may be selected from the group consisting of methotrexate, hydroxychloroquine, a CD20 antagonist (e.g., rituximab, ocrelizumab, beltuzumab, or ofatumumab), abatacept, a TNF antagonist (e.g., infliximab, adalimumab, and etanercept), sirolimus, and a BLyS antagonist (e.g., anti-BLyS (e.g., belimumab)).

The term "therapeutic agent for vasculitis" as used here may include a compound or composition that inhibits or treats symptoms associated with vasculitis. For the therapeutic agent for vasculitis, substances known in the art may be used.

The dosage and number of administration of the pharmaceutical composition may be determined according to the type of drug as an active ingredient, together with various related factors such as a disease to be treated, a route of administration, an age, a gender, and a weight of a patient, and severity of disease.

Since the pharmaceutical composition has excellent in vivo persistence and potency, the number and frequency of administration may be significantly reduced.

Another aspect provides a method of preventing or treating inflammatory or autoimmune disease, the method comprising administering the GIP derivative, the pharmaceutically acceptable salt or solvate thereof, the conjugate, or the pharmaceutical composition, in an effective amount to a subject in need thereof.

The GIP derivative, the pharmaceutically acceptable salt or solvate thereof, the conjugate, the pharmaceutical composition, and the inflammatory or autoimmune disease are the same as described above.

The term "effective amount" or "pharmaceutically effective amount" as used herein refers to an amount or quantity of the GIP derivative, the pharmaceutically acceptable salt or solvate thereof, or the conjugate, which can provide a desired effect to a patient under diagnosis or treatment when administered in a single dose or multiple doses. The effective amount may be readily determined by an attending diagnostician as a person skilled in the art by using known techniques or by observing results obtained under similar circumstances. When determining the effective amount for a patient, the mammalian species; the body size, age, and general health conditions of a patient; the specific disease or disorder involved; the degree or severity of involvement of the disease or disorder; the responsiveness in individual patients; the specific compound to be administered; the administration mode; the bioavailability characteristics of an agent to be administered; the selected dosing regimen; use of concomitant medication; and other relevant circumstances may be considered, but number of factors not limited thereto are also considered by an attending diagnostician.

The term "subject" as used herein refers to a target in need of treatment for a disease, and more particularly, to a mammal including a human or a non-human primate, such as a mouse, a rat, a dog, a cat, a horse, a cow, and the like.

The term "administration" as used herein refers to introduction of a given substance to a patient by any suitable method. The route of administration may be any general route capable of reaching a target in vivo in a patient. The administration may be, for example, intraperitoneal administration, intravenous administration, intramuscular administration, subcutaneous administration, intradermal administration, oral administration, topical administration, intranasal administration, or intrarectal administration, but embodiments are not limited thereto.

The composition according to an embodiment may be administered, at a daily rate per subject, in a range of 0.0001 mg to 1,000 mg, for example, 0.1 mg to 1,000 mg, 0.1 mg to 500 mg, 0.1 mg to 100 mg, 0.1 mg to 50 mg, 0.1 mg to 25 mg, 1 mg to 1,000 mg, 1 mg to 500 mg, 1 mg to 100 mg, 1 mg to 50 mg, or 1 mg to 25 mg. However, the dosage may be variously prescribed depending on factors, such as a formulation method, an administration method, age, weight, gender, and medical conditions of a patient, food, administration time, an administration route, an excretion rate, and response sensitivity, and a person skilled in the art may appropriate adjust the dosage in consideration of these factors. The number of administration may be once a day or at least twice a day within the range of clinically acceptable side effects, and the administration may be performed at a single site or at least two sites, daily or every 2 days to 5 days. The total number of administration days may be 1 day to 30 days per treatment. As needed, the same treatment may be repeated after a suitable period of time. For animals other than humans, the same dosage per kg as for humans may be used, or for example, a dosage converted from the aforementioned dosage by the volume ratio (e.g., average value) of the organ (e.g., heart, etc.) between a target animal and the human may be used.

In the method, the effective amount of the GIP derivative, the pharmaceutically acceptable salt or solvate thereof, or the conjugate thereof may be administered simultaneously, separately, or sequentially with the effective amount of one or more other active ingredients. The one or more other active ingredients may include one or more other agents for treating the inflammatory or autoimmune disease, but embodiments are not limited thereto.

Another aspect provides use of the GIP derivative, the pharmaceutically acceptable salt or solvate thereof, or the conjugate for use in the preparation of a drug for preventing or treating the inflammatory or autoimmune disease.

The GIP derivative, the pharmaceutically acceptable salt or solvate thereof, the conjugate, and the inflammatory or autoimmune disease are the same as described above.

Descriptions and embodiments disclosed herein may also be applied to other descriptions and embodiments, respectively. That is, all combinations of various elements disclosed herein belong to the scope of the present disclosure.

In addition, the scope of the present application is not construed to be limited by the detailed description provided below.

Advantageous Effects

A GIP derivative or a long-acting conjugate according to one aspect may have effects of decreasing expression levels of inflammation-related factors and decreasing expression levels of vascular remodeling factors in a vasculitis disease model, and thus can be utilized for use in prevention or treatment of vasculitis caused by inflammatory or autoimmune responses.

DESCRIPTION OF DRAWINGS

FIG. 1 is a diagram showing results of SDS-PAGE analysis on GIP derivative (SEQ ID NOs: 11, 17, 21, and 24)-PEG-immunoglobulin Fc region conjugates.

FIG. 2A is a graph showing the relative expression levels of inflammation-related genes IL-6, IL-12, IL-1beta, and TNF-alpha, after treated with a native GIP or a long-acting GIP conjugate.

FIG. 2B is a graph showing the concentration of inflammation-related cytokine, TNF-alpha, after treated with a native GIP or a long-acting GIP conjugate.

FIG. 4A is a graph showing the relative expression levels of inflammation-related genes MCP-1, IL-1β, IL-6, or TNF-α, in the renal arteries of a normal mouse control group, a disease model (MRL/lpr) mouse control group, a group administered with abatacept, and a group administered with a long-acting GIP conjugate.

FIG. 4B is a graph showing the relative expression levels of MMP-2 and MMP-9 that are known as vascular remodeling factors, in the renal arteries of a normal mouse control group, a disease model (MRL/lpr) mouse control group, a group administered with abatacept, and a group administered with a long-acting GIP conjugate.

BEST MODE

Figure 3:
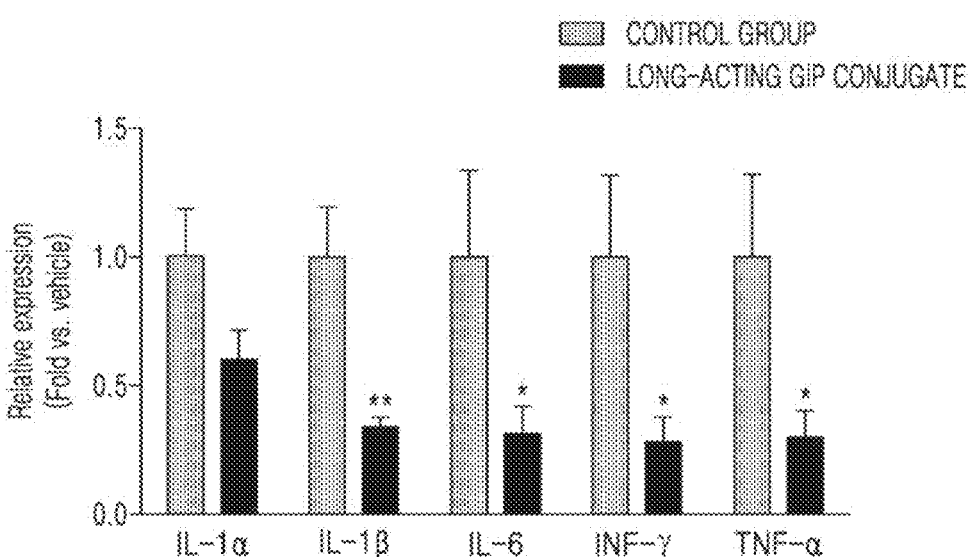
FIG. 3 is a graph showing the relative expression levels of inflammation-related genes IL-1α, IL-1β, IL-6, IFN-γ, and TNF-α, in a control group or a group administered with a long-acting conjugate.

Hereinafter, the present disclosure will be described in detail with reference to Examples below. However, these Examples are for illustrative purposes only, and the scope of the present disclosure is not intended to be limited by these Examples.

Example 1: Preparation of GIP Derivative Having Activity on GIP Receptor

GIP derivatives exhibiting activity on human GIP receptors were prepared, and sequences thereof are shown in Table 1.

TABLE 1

| SEQ ID NO. | Amino acid sequence |
|---|---|
| 1 | YAibEGT FISDY SIAMD AIAQQ DFVNW LLAQK PSSGA PPPSC |
| 2 | YAibEGT FISDY SIAMD AIAQQ DFVNW LLAGG PSSGA PPPSC |
| 3 | YAibEGT FISDY SIAibMD AIAQQ DFVNW LLAGG PSSGA PPPSC |
| 4 | YAibEGT FISDY SIYMD AIAQQ DFVNW LLAGG PSSGA PPPSC |
| 5 | YAibEGT FISDY SIQMD AIAQQ DFVNW LLAGG PSSGA PPPSC |
| 6 | YAibEGT FISDY SIYLD AIAQQ DFVNW LLAGG PSSGA PPPSC |
| 7 | YAibEGT FISDY SIYLD AQAQQ DFVNW LLAGG PSSGA PPPSC |
| 8 | YAibEGT FISDY SIYLD AQAAAib DFVNW LLAGG PSSGA PPPSC |
| 9 | YAibEGT FISDY SIYLD AQAAK DFVNW LLAGG PSSGA PPPSC |
| 10 | YAibEGT FISDY SIYLD AQAAK EFIAW LLAGG PSSGA PPPSC |
| 11 | YAibEGT FISDY SIAMD AIAQQ DFVNW LLAQK GKKND WKHNI TQC |
| 12 | YAibEGT FISDY SIYLD KQAAAib EFVNW LLAQK GKKND WKHNI TQC |
| 13 | YAibEGT FISDY SIYLD KQAAAib EFVNW LLAQK C |
| 14 | YAibEGT FISDY SIYLD AQAAAib EFVNW LLAQK C |
| 15 | YAibEGT FISDY SIAMD KIAQQ DFVNW LLAQK PSSGA PPPSC |
| 16 | YAibEGT FISDY SIAMD GIAQQ DFVNW LLAQK PSSGA PPPSC |

TABLE 1-continued

| SEQ ID NO. | Amino acid sequence |
|---|---|
| 17 | YAibEGT FISDY SIALE KQAQQ DFVNW LLAGG PSSGA PPPSC |
| 18 | YAibEGT FISDY SIYLD KQAAQ EFVNW LLAQK PSSGA PPPSC |
| 19 | YAibEGT FISDY SIYLD KQAAAib EFVNW LLAibGH PSSGA PPPSC |
| 20 | YAibEGT FISDY SIYLD KQAAAib EFVNW LLAibGG PSSGA PPPSC |
| 21 | YAibEGT FISDY SIAibLD KQAAAib EFVNW LLAibGG PSSGA PPPSC |
| 22 | YAibEGT FISDY SIYLD KQAAAib EFVNW LLAGH PSSGA PPPSC |
| 23 | YAibEGT FISDY SIYLD KQAQK EFVNW LLAibGG PSSGA PPPSC |
| 24 | YAibEGT FISDY SIAibLD KQAAAib EFVNW LLAibGH PSSGA PPPSC |
| 25 | YAibEGT FISDY SIYLD KQAAAib EFVQW LIAibGG PSSGA PPPSC |
| 26 | YAibEGT FISDY SIYLD KQAAAib EFVQW LIAGH PSSGA PPPC |

The amino acid indicated as Aib in the sequences shown in Table 1 is aminoisobutyric acid (Aib) which is a non-natural amino acid. The GIP derivative peptide may be used as a GIP derivative including amidated C-terminus, as needed.

Example 2: Measurement of In Vitro Activity of GIP Derivative

To measure the activity of the GIP derivatives prepared in Example 1, a method of measuring cell activity in vitro using a cell line transformed with the GIP receptor was used. The cell line was transformed to express each of human GIP receptor genes in the Chinese hamster ovary (CHO), and are suitable for the measurement of GIP activity.

To measure the activity of the GIP derivatives prepared in Example 1 in the human GIP receptors, human GIP was serially diluted from 16 nM to 0.000015 nM by 4 folds, and the GIP derivatives prepared in Example 1 were each serially diluted from 16 nM to 0.000015 nM by 4 folds. The culture medium was removed from the cultured CHO cells where the human GIP receptors were expressed, 5 μl of each of the serially diluted materials was added to the cells, and then, 5 μl of buffer containing cAMP antibody was added thereto, followed by incubation at room temperature for 15 minutes. Next, the cells were lysed by adding 10 μl of detection mix containing cell lysis buffer, and then allowed for a reaction at room temperature for 90 minutes. The cell lysate obtained by the completion of the reaction was applied to the LANGE cAMP kit (PerkinElmer, USA) to calculate the $EC_{50}$ value through the accumulated cAMP to be compared with each other.

Relative potencies compared to human GIP in the human GIP receptors are shown in Table 2.

TABLE 2

| SEQ ID NO. | In vitro activity of GIP derivative compared to human native GIP in human GIP receptor (%) |
|---|---|
| 1 | 49.3% |
| 2 | 13.9% |

TABLE 2-continued

| SEQ ID NO. | In vitro activity of GIP derivative compared to human native GIP in human GIP receptor (%) |
|---|---|
| 3 | 15.6% |
| 4 | 10.5% |
| 5 | 12.1% |
| 6 | 17.4% |
| 7 | 19.6% |
| 8 | 1.9% |
| 9 | 2.0% |
| 10 | 13.9% |
| 11 | 121.9% |
| 12 | 49.2% |
| 13 | 31.1% |
| 14 | 17.4% |
| 15 | 31.1% |
| 16 | 11.3% |
| 17 | 111.4% |
| 18 | 13.6% |
| 19 | 66.7% |
| 20 | 75.3% |
| 21 | 122.7% |
| 22 | 71.6% |
| 23 | 87.6% |
| 24 | 183.0% |
| 25 | 78.3% |
| 26 | 66.7% |

Example 3: Preparation of Long-Acting GIP Conjugate

A long-acting conjugate including the GIP derivative prepared in Example 1 was prepared. In detail, the GIP derivatives of SEQ ID NOs: 11, 17, 21 and 24 were each linked to an immunoglobulin Fc region through PEG which is a non-peptide polymer.

A specific manufacturing process of the long-acting conjugate is as follows, and the same process was repeated to prepare GIP derivative conjugates of SEQ ID NOs: 11, 17, 21 and 24. For pegylation at the N-terminus of the immunoglobulin Fc region, the immunoglobulin Fc region and MAL-10K PEG-ALD (10 kDa PEG having a maleimide group and a propionaldehyde group, respectively, at both ends, NOF, Japan) were reacted at a molar ratio of 1:1 to 2 at a total protein concentration in a range of 40 mg/ml to 60 mg/ml at a pH in a range of 6.0 to 6.5 for about 3 hours to about 4 hours at a temperature in a range of 4° C. to 8° C. Here, the reaction was carried out by adding sodium cyanoborohydride ($NaCNBH_3$) as a reducing agent, and reaction solution was subjected to the CaptoQ ImpRes (GE Healthcare Life Science, USA) column to purify mono-pegylated immunoglobulin Fc region.

Then, to link the purified mono-pegylated immunoglobulin Fc region to the GIP derivative, the mono-pegylated immunoglobulin Fc region and the GIP derivatives (SEQ ID NOs: 11, 17, 21, and 24) were reacted at a molar ratio of 1:1 to 3, at a total protein concentration in a range of 0.1 mg/ml to 0.5 mg/ml in an isopropanol-containing buffer for about 14 hours to about 18 hours at a temperature in a range of 4° C. to 8° C. The reaction solution was subjected to the Source 15ISO (GE Healthcare Life Science, USA) column to purify conjugates in which the GIP derivatives (SEQ ID NO: 11, 17, 21, and 24) were each covalently linked to the immunoglobulin Fc region by PEG.

As a result, a conjugate of purified GIP derivative of SEQ ID NO: 11-PEG-immunoglobulin Fc region, a conjugate of purified GIP derivative of SEQ ID NO: 17-PEG-immunoglobulin Fc region, a conjugate of purified GIP derivative of SEQ ID NO: 21-PEG-immunoglobulin Fc region, and a conjugate of purified GIP derivative of SEQ ID NO: 24-PEG-immunoglobulin Fc region were found to be prepared with a high purity of 90% or more, and results of SDS-PAGE analysis are shown in FIG. 1.

Example 4: Measurement of In Vitro Activity of Long-Acting GIP Conjugate

To measure the activity of the long-acting GIP conjugates prepared in Example 3, a method of measuring cell activity in vitro using a cell line transformed with the GIP receptor was used in the same manner as in Example 2.

In detail, to measure the activity of the long-acting GIP derivatives in the human GIP receptors, human GIP was serially diluted from 16 nM to 0.000015 nM by 4 folds, and the long-acting GIP derivatives prepared in Example 1 were each serially diluted from 50 nM to 0.000048 nM by 4 folds. The culture medium was removed from the cultured CHO cells where the human GIP receptors were expressed, 5 μl of each of the serially diluted materials was added to the cells, and then, 5 μl of buffer containing cAMP antibody was added thereto, followed by incubation at room temperature for 15 minutes. Next, the cells were lysed by adding 10 μl of detection mix containing cell lysis buffer, and then allowed for a reaction at room temperature for 90 minutes. The cell lysate obtained by the completion of the reaction was applied to the LANCE cAMP kit (PerkinElmer, USA) to calculate the $EC_{50}$ value through the accumulated cAMP to be compared with each other.

Relative potencies compared to human GIP in the human GIP receptors are shown in Table 3.

TABLE 3

| SEQ ID NO. | In vitro activity of long-acting GIP derivative compared to human native GIP in human GIP receptor (%) |
|---|---|
| 11 | 84.8% |
| 17 | 153.2% |

TABLE 3-continued

| SEQ ID NO. | In vitro activity of long-acting GIP derivative compared to human native GIP in human GIP receptor (%) |
|---|---|
| 21 | 148.5% |
| 24 | 123.3% |

In this Example, it was confirmed that the GIP derivative of the present disclosure retains the activity of native GIP, and especially when prepared in the form of the long-acting conjugate, not only the activity equivalent to or higher than that of native GIP, but also the increased half-life were exhibited, thereby showing excellent properties of the long-acting GIP derivative as a drug.

Example 5: Confirmation of In Vitro Anti-Inflammatory Effect of Long-Acting GIP Conjugate To confirm the in vitro anti-inflammatory effect of the long-acting GIP derivative conjugate on vasculitis, a human monocyte/macrophage cell line, THP-1 cell line, was used. A macrophage is known to secrete cytokines and chemokines in the early stage of infection in vasculitis-infected tissue, induce the progress of inflammation by utilizing other immune cells, and form giant cells. Therefore, identification of the anti-inflammatory effect in macrophages is referred to as an appropriate in vitro system for evaluating the efficacy on vasculitis.

The THP-1 cell line was cultured in RPMI 1640 medium supplemented with 10% fetal bovine serum (FBS), 100 μg/mL of streptomycin, 100 U/mL of penicillin, and 0.05 μm of β-mercaptoethanol, under conditions of a temperature of 37° C. and 5% carbon dioxide. An inflammatory response was induced by adding 1 μg/mL of lipopolysaccharide (LPS) to the cell line, and native GIP and the long-acting GIP derivative were treated thereon to confirm an effect thereof on the inflammatory response induced by LPS. When added, the native GIP was diluted to a concentration of 10 μM, and the long-acting GIP derivative was diluted to a concentration of 1 or 10 μM. For use as the long-acting GIP derivative, the long-acting GIP conjugate (SEQ ID NO: 17) prepared in Example 3 was used.

RNA was isolated from the completely treated THP-1 cell line by using the RNeasy Mini Kit (Qiagen, US), and then cDNA was synthesized by using the iScript™ cDNA Synthesis Kit (Bio-rad, U.S.). The synthesized cDNA was referred to confirm the expression levels of inflammation-related genes by using the QuantStudio 6 Flex Real-Time PCR System (Applied Biosystems, U.S.). Here, the Delta Ct method was used, and beta-actin was used as a housekeeping gene. IL-6, IL-12, IL-1β, and TNF-α were identified as inflammation-related genes.

Figure 2:
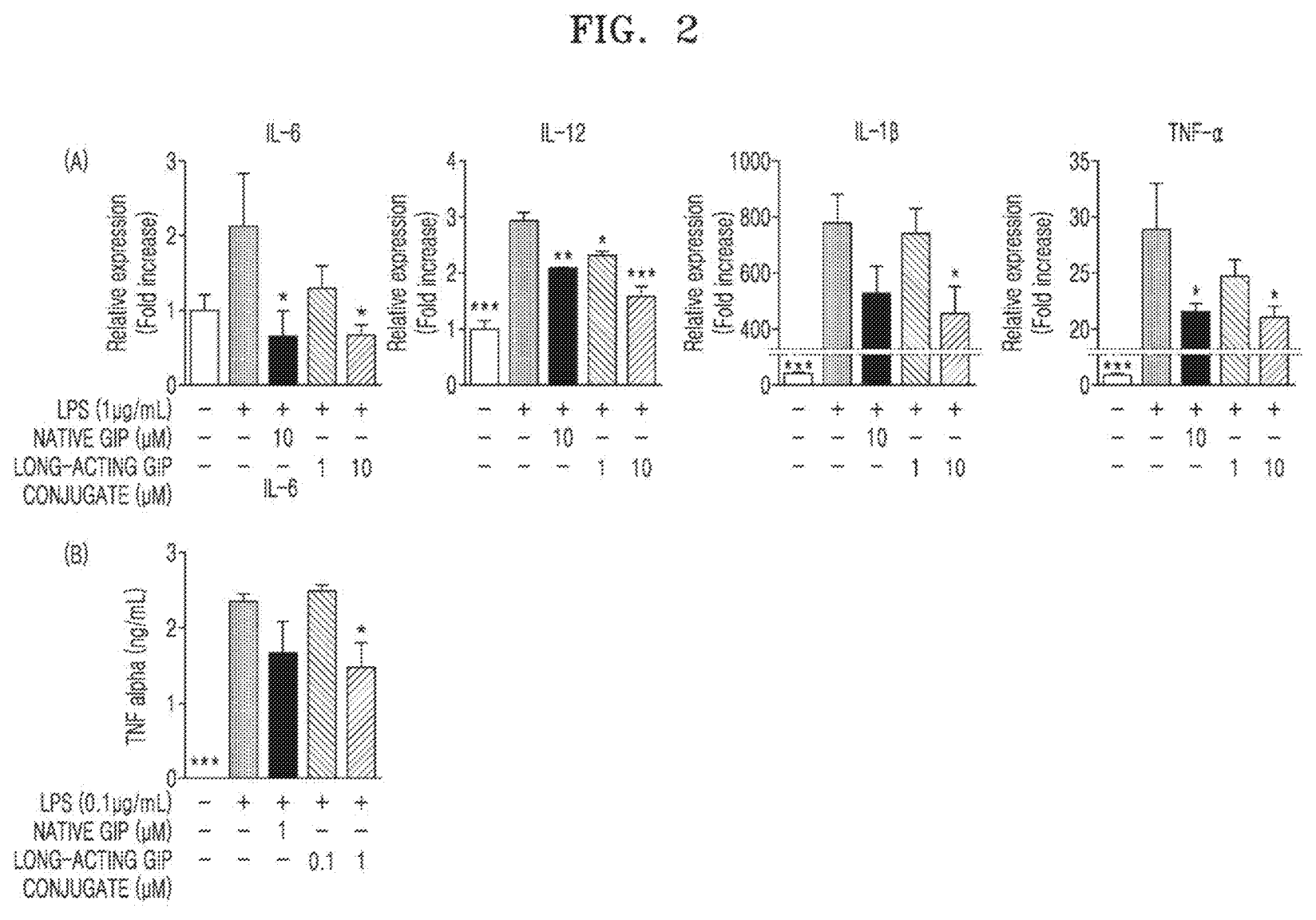

FIG. 2A is a graph showing the relative expression levels of the inflammation-related genes IL-6, IL-12, IL-1β, and TNF-α after treated with the native GIP or the long-acting GIP conjugate.

As shown in FIG. 2A, it was confirmed that the LPS treatment induced an inflammatory response and the expression levels of the inflammatory-related genes accordingly increased, and that the expression levels decreased again when treated with the native GIP and the long-acting GIP derivative. It was also confirmed that these results appeared in a concentration-dependent manner of the long-acting GIP derivative conjugate.

In addition, to measure the concentration of TNF-α, which is an inflammation-related cytokine, on the medium of the THP-1 cell line, an inflammatory response was induced by treatment with 0.1 pg/mL of LPS, and the native GIP was diluted to a concentration of 1 µM and the long-acting GIP derivative was diluted to a concentration of 0.1 µM or 1 µM for the treatment. Here, the medium was quantified by using Human TNF alpha ELISA Kit (Abcam, US).

FIG. 2B is a graph showing the concentration (ng/mL) of inflammation-related cytokine, TNF-α, after treated with the native GIP or the long-acting GIP conjugate.

As shown in FIG. 2B, it was confirmed that the concentration of TNF-α increased in the medium when treated with LPS, but decreased again when treated with the native GIP and the long-acting GIP conjugate.

Therefore, it was confirmed that the long-acting GIP conjugate directly acts on macrophages to exhibit an anti-inflammatory effect for preventing the response induced by LPS. Accordingly, it can be inferred from the results of the native GIP that such an anti-inflammatory effect is due to the action of the GIP.

Example 6: Confirmation of Anti-Inflammatory In Vivo Effect of Long-Acting GIP Conjugate In the same manner as in in vitro effect confirmed above, obese mice induced with a high-fat diet were used to confirm in vivo anti-inflammatory effect of the long-acting GIP derivative. The body weight of the mice was about 40 g to about 60 g before administration. During the study, the mice were housed in groups and had free access to water. The light was blocked from 6 AM to 6 PM.

A control group administered with an excipient and a test group administered with 11.7 nmol/kg of the long-acting GIP conjugate were prepared. The administration was performed at 2-day intervals, and the experiment was terminated on the 28th day. For use as the long-acting GIP conjugate, the long-acting GIP conjugate (SEQ ID NO: 17) prepared in Example 3 was used. After the experiment was terminated, the aorta was excised through autopsy, and RNA was extracted therefrom. RNA was extracted by using the RNeasy Mini Kit (Qiagen, US), and cDNA was synthesized by using the iScript™ cDNA Synthesis Kit (Bio-rad, U.S.). The synthesized cDNA was referred to confirm the expression levels of inflammation-related genes by using the QuantStudio 6 Flex Real-Time PCR System (Applied Biosystems, U.S.), and the difference between the control group and the test group was compared.

FIG. 3 is a graph showing the relative expression levels of inflammation-related genes IL-1α, IL-1β, IL-6, IFN-γ, and TNF-α, in the control group or the test group administered with the long-acting conjugate.

As shown in FIG. 3, as a result of measuring the expression levels of inflammation-related genes, it was confirmed that the expression of all the inflammation-related genes was significantly reduced in the test group administered with the long-acting GIP conjugate compared to the control group. Therefore, it was confirmed that the long-acting GIP conjugate has an excellent anti-inflammatory effect.

Example 7: Confirmation of Efficacy of Long-Acting GIP Conjugate in Vasculitis Disease Model To confirm efficacy of the long-acting GIP conjugate on vasculitis in a disease model, MRL/lpr mice were used. In the case of the mice, it is known that vasculitis is observed in the large vessels including the aorta and major branches caused by systemic inflammation (Arthritis Rheum. 2003 May; 48(5):1445-51). Therefore, the mice of this type were selected as a vasculitis disease model.

There are a normal mouse control group administered with an excipient, a disease mouse control group administered with an excipient, a control group administered with commercially available abatacept (Orencia, Inc.,) at a concentration of 5.7 mg/kg, and test groups each administered with the long-acting GIP conjugate at a concentration of 0.12 mg/kg, 1.05 mg/kg, or 3.16 mg/kg. The administration of the excipient and the drugs was performed at 2-day intervals, and the experiment was terminated at the 10th week. For use as the long-acting GIP conjugate, the long-acting GIP conjugate (SEQ ID NO: 17) prepared in Example 3 was used.

FIG. 4A is a graph showing the relative expression levels of inflammation-related genes MCP-1, IL-1β, IL-6, or TNF-α, in the renal arteries of the normal mouse control group, the disease model (MRL/lpr) mouse control group, the control group administered with abatacept, and the group administered with the long-acting GIP conjugate.

As shown in FIG. 4A, as a result of measuring the expression levels of inflammation-related genes, it was confirmed that the expression of all the inflammation-related genes was significantly reduced in the control group administered with abatacept and the test group administered with the long-acting GIP conjugate, compared to the control groups of disease model.

FIG. 4B is a graph showing the relative expression levels of MMP-2 and MMP-9 that are known as vascular remodeling factors, in the renal arteries of the normal mouse control group, the disease model (MRL/lpr) mouse control group, the control group administered with abatacept, and the group administered with the long-acting GIP conjugate.

As shown in FIG. 4B, it was confirmed that, unlike the case of abatacept, the test group administered with the long-acting GIP conjugate had a tendency to decrease the expression of vascular remodeling genes compared to the control groups.

Therefore, it was confirmed that the long-acting GIP conjugate directly acts on blood vessels in the control group of disease model not only to exhibit an anti-inflammatory effect for preventing the inflammatory response, but also to lower the expression of vascular remodeling factors that play an important role in the progression of vasculitis.

Example 8: Confirmation of Efficacy of Long-Acting GIP Conjugate in Angiotensin II-Infused Mice To confirm efficacy of the long-acting GIP conjugate on vasculitis in a disease model, angiotensin II infused mice (AngII mice) were used. The AngII mice were normal mice (male C57BL/6N mice, DBL Co., Ltd.) to which 1.4 mg of AngII (Sigma-Aldrich) was administered every day for 4 weeks. In the case of the mice, the mice are known as a disease model for hypertension, but it is also known that the wall of the artery of the mouse is inflamed and thickened by AngII (Hypertension. 2004, 44:264-270). Therefore, the mice of this type were selected as a vasculitis disease model. During the study, the mice were housed in groups and had free access to water. The light was blocked from 6 AM to 6 PM.

A normal mouse control group (Control, male C57BL/6N mice, DBL Co., Ltd.) and a control group of disease model (AngII) were administered with an excipient. Test groups were each administered with the long-acting GIP conjugate at a concentration of 3.163 mg/kg. Administration of the excipient and the long-acting GIP conjugate was administered at 2-day intervals, and the experiment was terminated on the 4th week. For use as the long-acting GIP conjugate, the long-acting GIP conjugate (SEQ ID NO: 17) prepared in Example 3 was used.

After the experiment was terminated, the two aortas, i.e., the arch of the aorta and the abdominal aorta, were excised through autopsy, and RNA was extracted therefrom. RNA was extracted by using the RNeasy Mini Kit (Qiagen, US), and cDNA was synthesized by using the iScript™ cDNA Synthesis Kit (Bio-rad, U.S.). The synthesized cDNA was referred to confirm and compare the expression levels of inflammation-related genes by using the QuantStudio 6 Flex Real-Time PCR System (Applied Biosystems, U. S.).

Figure 5:
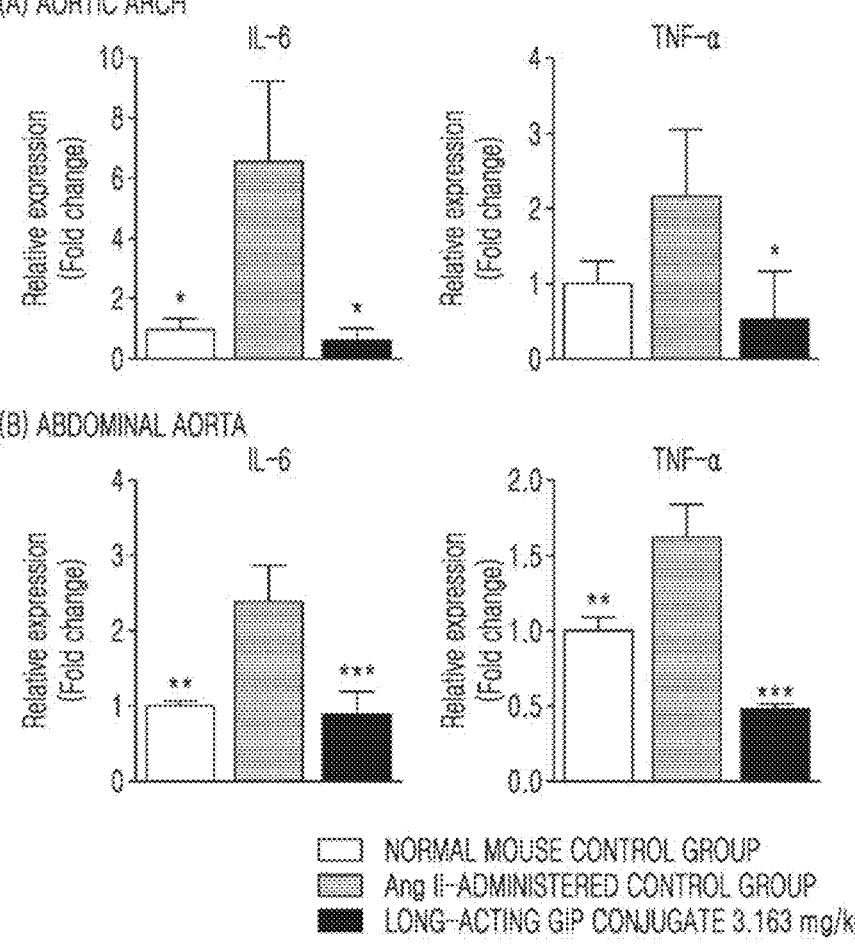
FIG. 5A is a graph showing the relative expression levels of IL-6 and TNF-α genes, in the aortic arch of a normal mouse control group, a disease model mouse control group (e.g., an AngII-administered control group), and a test group (administered with long-acting GIP conjugate at a concentration of 3.163 mg/kg).
FIG. 5B is a graph showing the relative expression levels of IL-6 and TNF-α genes, in the abdominal aorta of a normal mouse control group, a disease model mouse control group (e.g., an AngII-administered control group), and a test group (administered with long-acting GIP conjugate at a concentration of 3.163 mg/kg).

FIG. 5A is a graph showing the relative expression levels of IL-6 and TNF-α genes, in the aortic arch of a normal mouse control group, a control group of disease model mice (i.e., an AngII-administered control group), and a test group (administered with long-acting GIP conjugate at a concentration of 3.163 mg/kg).

FIG. 5B is a graph showing the relative expression levels of IL-6 and TNF-α genes, in the abdominal aorta of a normal mouse control group, a control group of disease model mice (i.e., an AngII-administered control group), and a test group (administered with long-acting GIP conjugate at a concentration of 3.163 mg/kg).

As a result, as shown in FIGS. 5A and 5B, it was confirmed that the expression of IL-6 and TNF-α genes in the test group administered with the long-acting GIP conjugate in both aortas decreased compared to that in the control group of the disease model.

Therefore, it was confirmed that the long-acting GIP conjugate directly acts on the aorta in the disease model and reduces the expression of the inflammation-related genes, thereby exhibiting the anti-inflammatory effect that prevents the inflammatory response.

The invention claimed is:

1. A peptide comprising any one amino acid sequence selected from the group consisting of SEQ ID NOs: 1 to 26.

2. The peptide of claim 1, wherein the peptide has activity on a glucose-dependent insulinotropic peptide (GIP) receptor.

3. The peptide of claim 1, wherein the peptide comprises any one amino acid sequence selected from the group consisting of SEQ ID NOs: 11, 17, and 19 to 26.

4. The peptide of claim 1, wherein the peptide comprises any one amino acid sequence selected from the group consisting of SEQ ID NOs: 11, 17, 21, and 24.

5. The peptide of claim 1, wherein the C-terminus of the peptide is not modified or is amidated.

6. The peptide of claim 1, wherein the peptide is conjugated to a moiety that increases half-life in vivo.

7. The peptide of claim 6, wherein the moiety is selected from the group consisting of polyethylene glycol, polypropylene glycol, ethylene glycol-propylene glycol copolymer, polyoxyethylated polyol, polyvinyl alcohol, polysaccharide, polyvinyl ethyl ether, a biodegradable polymer, a lipid polymer, chitin, hyaluronic acid, fatty acid, cholesterol, albumin or fragment thereof, an albumin-binding molecule, a polymer of repeating units of specific amino acid sequences, an antibody, an antibody fragment, an FcRn-binding molecule, fibronectin, transferrin, a saccharide, heparin, elastin, and combination thereof.

8. The peptide of claim 6, wherein the moiety is an FcRn-binding molecule.

9. The peptide of claim 8, wherein the FcRn-binding molecule is an immunoglobulin Fc region.

10. The peptide of claim 9, wherein the immunoglobulin Fc region is selected from the group consisting of: (a) a heavy-chain constant region 1 (CH1) domain, a heavy-chain constant region 2 (CH2) domain, a heavy-chain constant region 3 (CH3) domain, and a heavy-chain constant region 4 (CH4) domain; (b) a CH1 domain and a CH2 domain; (c) a CH1 domain and a CH3 domain; (d) a CH2 domain and a CH3 domain; (e) a combination between one or two or more domains among a CH1 domain, a CH2 domain, a CH3 domain, and a CH4 domain, and an immunoglobulin hinge region or a part of the hinge region; and (f) a dimer between each domain of the heavy chain constant region and the light chain constant region.

11. The peptide of claim 9, wherein the immunoglobulin Fc region is aglycosylated.

12. The peptide of claim 9, wherein the immunoglobulin Fc region is an immunoglobulin G4 (IgG4) Fc region.

13. The peptide of claim 9, wherein the immunoglobulin Fc region is aglycosylated Fc region derived from human IgG4.

14. The peptide of claim 6, wherein the peptide is linked to the moiety via a linker.

15. The peptide of claim 14, wherein the linker is selected from the group consisting of a peptide, a fatty acid, a saccharide, a polyethylene glycol, a polypropylene glycol, an ethylene glycol-propylene glycol copolymer, a polyoxyethylated polyol, a polyvinyl alcohol, a polysaccharide, a polyvinyl ethyl ether, a biodegradable polymer, a lipid polymer, chitin, hyaluronic acid, an oligonucleotide, and a combination thereof.

16. The peptide of claim 14, wherein the linker comprises an ethylene glycol repeating unit.

17. The peptide of claim 16, wherein the ethylene glycol repeating unit has a molecular weight in a range of 1 kDa to 100 kDa.

18. A pharmaceutical composition comprising the peptide of claim 1, a pharmaceutically acceptable salt thereof or a solvate thereof.

19. The pharmaceutical composition of claim 18, wherein the peptide is conjugated to a moiety that increases half-life in vivo.

20. A method for treating vasculitis, rheumatoid arthritis, or diabetes mellitus in a subject in need thereof, wherein the method comprises administering to the subject a pharmaceutical composition comprising a therapeutically effective amount of a peptide comprising any one amino acid sequence selected from the group consisting of SEQ ID NOs: 11, 17, 21 and 24.

21. The method of claim 20, wherein the vasculitis is one selected from the group consisting of: giant cell arteritis; Takayasu's arteritis; aortitis in Cogan's syndrome; aortitis in spondylarthropathies; isolated aortitis; Kawasaki disease; polyarteritis nodosa; antineutrophil cytoplasmic antibodies (ANCA)-associated vasculitis; granulomatosis with polyangiitis; microscopic polyangiitis; eosinophilic granulomatosis with polyangiitis; primary angiitis of the central nervous system; IgA vasculitis; vasculitis associated with rheumatoid arthritis, vasculitis associated with systemic lupus erythematosus, vasculitis associated with Sjogren's syndrome; cryoglobulinemic vasculitis; and drug-induced vasculitis.

22. The method of claim 20, wherein the peptide is conjugated to a moiety that increases half-life in vivo.

* * * * *

SEQUENCE LISTING

```
<160> NUMBER OF SEQ ID NOS: 60

<210> SEQ ID NO 1
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 1

Tyr Xaa Glu Gly Thr Phe Ile Ser Asp Tyr Ser Ile Ala Met Asp Ala
1               5                   10                  15

Ile Ala Gln Gln Asp Phe Val Asn Trp Leu Leu Ala Gln Lys Pro Ser
            20                  25                  30

Ser Gly Ala Pro Pro Pro Ser Cys
        35                  40

<210> SEQ ID NO 2
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 2

Tyr Xaa Glu Gly Thr Phe Ile Ser Asp Tyr Ser Ile Ala Met Asp Ala
1               5                   10                  15

Ile Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 3
<211> LENGTH: 40
<212> TYPE: PRT
<213> ORGANISM: Artificial
<220> FEATURE:
```

```
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (13)..(13)
<223> OTHER INFORMATION: Xaa is aminoisobutyric acid (Aib)

<400> SEQUENCE: 3

Tyr Xaa Glu Gly Thr Phe Ile Ser Asp Tyr Ser Ile Xaa Met Asp Ala
1               5                   10                  15

Ile Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 4
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 4

Tyr Xaa Glu Gly Thr Phe Ile Ser Asp Tyr Ser Ile Tyr Met Asp Ala
1               5                   10                  15

Ile Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 5
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 5

Tyr Xaa Glu Gly Thr Phe Ile Ser Asp Tyr Ser Ile Gln Met Asp Ala
1               5                   10                  15

Ile Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 6
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
```

-continued

```
<400> SEQUENCE: 6

Tyr Xaa Glu Gly Thr Phe Ile Ser Asp Tyr Ser Ile Tyr Leu Asp Ala
1               5                   10                  15

Ile Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 7
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 7

Tyr Xaa Glu Gly Thr Phe Ile Ser Asp Tyr Ser Ile Tyr Leu Asp Ala
1               5                   10                  15

Gln Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 8
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)

<400> SEQUENCE: 8

Tyr Xaa Glu Gly Thr Phe Ile Ser Asp Tyr Ser Ile Tyr Leu Asp Ala
1               5                   10                  15

Gln Ala Ala Xaa Asp Phe Val Asn Trp Leu Leu Ala Gly Gly Pro Ser
            20                  25                  30

Ser Gly Ala Pro Pro Pro Ser Cys
        35                  40

<210> SEQ ID NO 9
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 9

Tyr Xaa Glu Gly Thr Phe Ile Ser Asp Tyr Ser Ile Tyr Leu Asp Ala
1               5                   10                  15

Gln Ala Ala Lys Asp Phe Val Asn Trp Leu Leu Ala Gly Gly Pro Ser
```

-continued

```
                20                  25                  30

Ser Gly Ala Pro Pro Pro Ser Cys
        35                  40

<210> SEQ ID NO 10
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 10

Tyr Xaa Glu Gly Thr Phe Ile Ser Asp Tyr Ser Ile Tyr Leu Asp Ala
1               5                   10                  15

Gln Ala Ala Lys Glu Phe Ile Ala Trp Leu Leu Ala Gly Gly Pro Ser
            20                  25                  30

Ser Gly Ala Pro Pro Pro Ser Cys
        35                  40

<210> SEQ ID NO 11
<211> LENGTH: 43
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 11

Tyr Xaa Glu Gly Thr Phe Ile Ser Asp Tyr Ser Ile Ala Met Asp Ala
1               5                   10                  15

Ile Ala Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 12
<211> LENGTH: 43
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)

<400> SEQUENCE: 12

Tyr Xaa Glu Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gln Lys Gly Lys
            20                  25                  30

Lys Asn Asp Trp Lys His Asn Ile Thr Gln Cys
        35                  40
```

-continued

```
<210> SEQ ID NO 13
<211> LENGTH: 31
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)

<400> SEQUENCE: 13

Tyr Xaa Glu Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gln Lys Cys
            20                  25                  30

<210> SEQ ID NO 14
<211> LENGTH: 31
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)

<400> SEQUENCE: 14

Tyr Xaa Glu Gly Thr Phe Ile Ser Asp Tyr Ser Ile Tyr Leu Asp Ala
1               5                   10                  15

Gln Ala Ala Xaa Glu Phe Val Asn Trp Leu Leu Ala Gln Lys Cys
            20                  25                  30

<210> SEQ ID NO 15
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 15

Tyr Xaa Glu Gly Thr Phe Ile Ser Asp Tyr Ser Ile Ala Met Asp Lys
1               5                   10                  15

Ile Ala Gln Gln Asp Phe Val Asn Trp Leu Leu Ala Gln Lys Pro Ser
            20                  25                  30

Ser Gly Ala Pro Pro Pro Ser Cys
        35                  40

<210> SEQ ID NO 16
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
```

-continued

```
<222> LOCATION: (2)..(2)
<223> OTHER INFORMATION: Xaa is aminoisobutyric acid (Aib)

<400> SEQUENCE: 16

Tyr Xaa Glu Gly Thr Phe Ile Ser Asp Tyr Ser Ile Ala Met Asp Gly
1               5                   10                  15

Ile Ala Gln Gln Asp Phe Val Asn Trp Leu Leu Ala Gln Lys Pro Ser
            20                  25                  30

Ser Gly Ala Pro Pro Pro Ser Cys
        35                  40

<210> SEQ ID NO 17
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 17

Tyr Xaa Glu Gly Thr Phe Ile Ser Asp Tyr Ser Ile Ala Leu Glu Lys
1               5                   10                  15

Gln Ala Gln Gln Asp Phe Val Asn Trp Leu Leu Ala Gly Gly Pro Ser
            20                  25                  30

Ser Gly Ala Pro Pro Pro Ser Cys
        35                  40

<210> SEQ ID NO 18
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 18

Tyr Xaa Glu Gly Thr Phe Ile Ser Asp Tyr Ser Ile Tyr Leu Asp Lys
1               5                   10                  15

Gln Ala Ala Gln Glu Phe Val Asn Trp Leu Leu Ala Gln Lys Pro Ser
            20                  25                  30

Ser Gly Ala Pro Pro Pro Ser Cys
        35                  40

<210> SEQ ID NO 19
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)
<220> FEATURE:
<221> NAME/KEY: MISC_FEATURE
<222> LOCATION: (28)..(28)
<223> OTHER INFORMATION: Xaa is aminoisobutyric acid (Aib)
```

<400> SEQUENCE: 19

Tyr Xaa Glu Gly Thr Phe Ile Ser Asp Tyr Ser Ile Tyr Leu Asp Lys
1               5                   10                  15

Gln Ala Ala Xaa Glu Phe Val Asn Trp Leu Leu Xaa Gly His Pro Ser
            20                  25                  30

Ser Gly Ala Pro Pro Pro Ser Cys
        35                  40

<210> SEQ ID NO 20
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)
<220> FEATURE:
<221> NAME/KEY: MISC_FEATURE
<222> LOCATION: (28)..(28)
<223> OTHER INFORMATION: Xaa is aminoisobutyric acid (Aib)

<400> SEQUENCE: 20

Tyr Xaa Glu Gly Thr Phe Ile Ser Asp Tyr Ser Ile Tyr Leu Asp Lys
1               5                   10                  15

Gln Ala Ala Xaa Glu Phe Val Asn Trp Leu Leu Xaa Gly Gly Pro Ser
            20                  25                  30

Ser Gly Ala Pro Pro Pro Ser Cys
        35                  40

<210> SEQ ID NO 21
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (13)..(13)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)
<220> FEATURE:
<221> NAME/KEY: MISC_FEATURE
<222> LOCATION: (28)..(28)
<223> OTHER INFORMATION: Xaa is aminoisobutyric acid (Aib)

<400> SEQUENCE: 21

Tyr Xaa Glu Gly Thr Phe Ile Ser Asp Tyr Ser Ile Xaa Leu Asp Lys
1               5                   10                  15

Gln Ala Ala Xaa Glu Phe Val Asn Trp Leu Leu Xaa Gly Gly Pro Ser
            20                  25                  30

Ser Gly Ala Pro Pro Pro Ser Cys
        35                  40

-continued

```
<210> SEQ ID NO 22
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)

<400> SEQUENCE: 22

Tyr Xaa Glu Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gly His Pro Ser
            20                  25                  30

Ser Gly Ala Pro Pro Pro Ser Cys
        35                  40

<210> SEQ ID NO 23
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (28)..(28)
<223> OTHER INFORMATION: Xaa is aminoisobutyric acid (Aib)

<400> SEQUENCE: 23

Tyr Xaa Glu Gly Thr Phe Ile Ser Asp Tyr Ser Ile Tyr Leu Asp Lys
1               5                   10                  15

Gln Ala Gln Lys Glu Phe Val Asn Trp Leu Leu Xaa Gly Gly Pro Ser
            20                  25                  30

Ser Gly Ala Pro Pro Pro Ser Cys
        35                  40

<210> SEQ ID NO 24
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (13)..(13)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)
<220> FEATURE:
<221> NAME/KEY: MISC_FEATURE
<222> LOCATION: (28)..(28)
<223> OTHER INFORMATION: Xaa is aminoisobutyric acid (Aib)

<400> SEQUENCE: 24
```

-continued

```
Tyr Xaa Glu Gly Thr Phe Ile Ser Asp Tyr Ser Ile Xaa Leu Asp Lys
1               5                   10                  15

Gln Ala Ala Xaa Glu Phe Val Asn Trp Leu Leu Xaa Gly His Pro Ser
            20                  25                  30

Ser Gly Ala Pro Pro Pro Ser Cys
        35                  40
```

<210> SEQ ID NO 25
<211> LENGTH: 40
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)
<220> FEATURE:
<221> NAME/KEY: MISC_FEATURE
<222> LOCATION: (28)..(28)
<223> OTHER INFORMATION: Xaa is aminoisobutyric acid (Aib)

<400> SEQUENCE: 25

```
Tyr Xaa Glu Gly Thr Phe Ile Ser Asp Tyr Ser Ile Tyr Leu Asp Lys
1               5                   10                  15

Gln Ala Ala Xaa Glu Phe Val Gln Trp Leu Ile Xaa Gly Gly Pro Ser
            20                  25                  30

Ser Gly Ala Pro Pro Pro Ser Cys
        35                  40
```

<210> SEQ ID NO 26
<211> LENGTH: 39
<212> TYPE: PRT
<213> ORGANISM: Artificial
<220> FEATURE:
<223> OTHER INFORMATION: GIP derivative
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (20)..(20)
<223> OTHER INFORMATION: Xaa is aminoisobutyric acid (Aib)

<400> SEQUENCE: 26

```
Tyr Xaa Glu Gly Thr Phe Ile Ser Asp Tyr Ser Ile Tyr Leu Asp Lys
1               5                   10                  15

Gln Ala Ala Xaa Glu Phe Val Gln Trp Leu Ile Ala Gly His Pro Ser
            20                  25                  30

Ser Gly Ala Pro Pro Pro Cys
        35
```

<210> SEQ ID NO 27
<211> LENGTH: 12
<212> TYPE: PRT
<213> ORGANISM: Homo sapiens

<400> SEQUENCE: 27

```
Glu Ser Lys Tyr Gly Pro Pro Cys Pro Ser Cys Pro
1               5                   10
```

```
<210> SEQ ID NO 28
<211> LENGTH: 11
<212> TYPE: PRT
<213> ORGANISM: Artificial
<220> FEATURE:
<223> OTHER INFORMATION: Variant of hinge region

<400> SEQUENCE: 28

Glu Ser Lys Tyr Gly Pro Pro Pro Ser Cys Pro
1               5                   10

<210> SEQ ID NO 29
<211> LENGTH: 11
<212> TYPE: PRT
<213> ORGANISM: Artificial
<220> FEATURE:
<223> OTHER INFORMATION: Variant of hinge region

<400> SEQUENCE: 29

Glu Ser Lys Tyr Gly Pro Pro Cys Pro Ser Pro
1               5                   10

<210> SEQ ID NO 30
<211> LENGTH: 10
<212> TYPE: PRT
<213> ORGANISM: Artificial
<220> FEATURE:
<223> OTHER INFORMATION: Variant of hinge region

<400> SEQUENCE: 30

Glu Ser Lys Tyr Gly Pro Pro Cys Pro Ser
1               5                   10

<210> SEQ ID NO 31
<211> LENGTH: 10
<212> TYPE: PRT
<213> ORGANISM: Artificial
<220> FEATURE:
<223> OTHER INFORMATION: Variant of hinge region

<400> SEQUENCE: 31

Glu Ser Lys Tyr Gly Pro Pro Cys Pro Pro
1               5                   10

<210> SEQ ID NO 32
<211> LENGTH: 8
<212> TYPE: PRT
<213> ORGANISM: Artificial
<220> FEATURE:
<223> OTHER INFORMATION: Variant of hinge region

<400> SEQUENCE: 32

Lys Tyr Gly Pro Pro Cys Pro Ser
1               5

<210> SEQ ID NO 33
<211> LENGTH: 8
<212> TYPE: PRT
<213> ORGANISM: Artificial
<220> FEATURE:
<223> OTHER INFORMATION: Variant of hinge region

<400> SEQUENCE: 33

Glu Ser Lys Tyr Gly Pro Pro Cys
1               5

<210> SEQ ID NO 34
```

-continued

```
<211> LENGTH: 7
<212> TYPE: PRT
<213> ORGANISM: Artificial
<220> FEATURE:
<223> OTHER INFORMATION: Variant of hinge region

<400> SEQUENCE: 34

Glu Lys Tyr Gly Pro Pro Cys
1               5

<210> SEQ ID NO 35
<211> LENGTH: 6
<212> TYPE: PRT
<213> ORGANISM: Artificial
<220> FEATURE:
<223> OTHER INFORMATION: Variant of hinge region

<400> SEQUENCE: 35

Glu Ser Pro Ser Cys Pro
1               5

<210> SEQ ID NO 36
<211> LENGTH: 5
<212> TYPE: PRT
<213> ORGANISM: Artificial
<220> FEATURE:
<223> OTHER INFORMATION: Variant of hinge region

<400> SEQUENCE: 36

Glu Pro Ser Cys Pro
1               5

<210> SEQ ID NO 37
<211> LENGTH: 4
<212> TYPE: PRT
<213> ORGANISM: Artificial
<220> FEATURE:
<223> OTHER INFORMATION: Variant of hinge region

<400> SEQUENCE: 37

Pro Ser Cys Pro
1

<210> SEQ ID NO 38
<211> LENGTH: 10
<212> TYPE: PRT
<213> ORGANISM: Artificial
<220> FEATURE:
<223> OTHER INFORMATION: Variant of hinge region

<400> SEQUENCE: 38

Glu Ser Lys Tyr Gly Pro Pro Ser Cys Pro
1               5                   10

<210> SEQ ID NO 39
<211> LENGTH: 9
<212> TYPE: PRT
<213> ORGANISM: Artificial
<220> FEATURE:
<223> OTHER INFORMATION: Variant of hinge region

<400> SEQUENCE: 39

Lys Tyr Gly Pro Pro Pro Ser Cys Pro
1               5

<210> SEQ ID NO 40
<211> LENGTH: 9
```

```
<212> TYPE: PRT
<213> ORGANISM: Artificial
<220> FEATURE:
<223> OTHER INFORMATION: Variant of hinge region

<400> SEQUENCE: 40

Glu Ser Lys Tyr Gly Pro Ser Cys Pro
1               5

<210> SEQ ID NO 41
<211> LENGTH: 8
<212> TYPE: PRT
<213> ORGANISM: Artificial
<220> FEATURE:
<223> OTHER INFORMATION: Variant of hinge region

<400> SEQUENCE: 41

Glu Ser Lys Tyr Gly Pro Pro Cys
1               5

<210> SEQ ID NO 42
<211> LENGTH: 7
<212> TYPE: PRT
<213> ORGANISM: Artificial
<220> FEATURE:
<223> OTHER INFORMATION: Variant of hinge region

<400> SEQUENCE: 42

Lys Tyr Gly Pro Pro Cys Pro
1               5

<210> SEQ ID NO 43
<211> LENGTH: 7
<212> TYPE: PRT
<213> ORGANISM: Artificial
<220> FEATURE:
<223> OTHER INFORMATION: Variant of hinge region

<400> SEQUENCE: 43

Glu Ser Lys Pro Ser Cys Pro
1               5

<210> SEQ ID NO 44
<211> LENGTH: 6
<212> TYPE: PRT
<213> ORGANISM: Artificial
<220> FEATURE:
<223> OTHER INFORMATION: Variant of hinge region

<400> SEQUENCE: 44

Glu Ser Pro Ser Cys Pro
1               5

<210> SEQ ID NO 45
<211> LENGTH: 4
<212> TYPE: PRT
<213> ORGANISM: Artificial
<220> FEATURE:
<223> OTHER INFORMATION: Variant of hinge region

<400> SEQUENCE: 45

Glu Pro Ser Cys
1

<210> SEQ ID NO 46
<211> LENGTH: 3
<212> TYPE: PRT
```

-continued

```
<213> ORGANISM: Artificial
<220> FEATURE:
<223> OTHER INFORMATION: Variant of hinge region

<400> SEQUENCE: 46

Ser Cys Pro
1

<210> SEQ ID NO 47
<211> LENGTH: 5
<212> TYPE: PRT
<213> ORGANISM: Artificial
<220> FEATURE:
<223> OTHER INFORMATION: Synthetic construct (linker)

<400> SEQUENCE: 47

Gly Gly Gly Gly Ser
1               5

<210> SEQ ID NO 48
<211> LENGTH: 5
<212> TYPE: PRT
<213> ORGANISM: Artificial
<220> FEATURE:
<223> OTHER INFORMATION: Synthetic construct (linker)

<400> SEQUENCE: 48

Ser Gly Gly Gly Gly
1               5

<210> SEQ ID NO 49
<211> LENGTH: 5
<212> TYPE: PRT
<213> ORGANISM: Artificial
<220> FEATURE:
<223> OTHER INFORMATION: Synthetic construct (linker)

<400> SEQUENCE: 49

Ser Arg Ser Ser Gly
1               5

<210> SEQ ID NO 50
<211> LENGTH: 5
<212> TYPE: PRT
<213> ORGANISM: Artificial
<220> FEATURE:
<223> OTHER INFORMATION: Synthetic construct (linker)

<400> SEQUENCE: 50

Ser Gly Ser Ser Cys
1               5

<210> SEQ ID NO 51
<211> LENGTH: 12
<212> TYPE: PRT
<213> ORGANISM: Artificial
<220> FEATURE:
<223> OTHER INFORMATION: Synthetic construct (linker)

<400> SEQUENCE: 51

Gly Lys Ser Ser Gly Ser Gly Ser Glu Ser Lys Ser
1               5                   10

<210> SEQ ID NO 52
<211> LENGTH: 6
<212> TYPE: PRT
<213> ORGANISM: Artificial
```

<220> FEATURE:
<223> OTHER INFORMATION: Synthetic construct (linker)

<400> SEQUENCE: 52

Arg Pro Pro Pro Pro Cys
1               5

<210> SEQ ID NO 53
<211> LENGTH: 7
<212> TYPE: PRT
<213> ORGANISM: Artificial
<220> FEATURE:
<223> OTHER INFORMATION: Synthetic construct (linker)

<400> SEQUENCE: 53

Ser Ser Pro Pro Pro Pro Cys
1               5

<210> SEQ ID NO 54
<211> LENGTH: 14
<212> TYPE: PRT
<213> ORGANISM: Artificial
<220> FEATURE:
<223> OTHER INFORMATION: Synthetic construct (linker)

<400> SEQUENCE: 54

Gly Ser Thr Ser Gly Ser Gly Lys Ser Ser Glu Gly Lys Gly
1               5                   10

<210> SEQ ID NO 55
<211> LENGTH: 18
<212> TYPE: PRT
<213> ORGANISM: Artificial
<220> FEATURE:
<223> OTHER INFORMATION: Synthetic construct (linker)

<400> SEQUENCE: 55

Gly Ser Thr Ser Gly Ser Gly Lys Ser Ser Glu Gly Ser Gly Ser Thr
1               5                   10                  15

Lys Gly

<210> SEQ ID NO 56
<211> LENGTH: 18
<212> TYPE: PRT
<213> ORGANISM: Artificial
<220> FEATURE:
<223> OTHER INFORMATION: Synthetic construct (linker)

<400> SEQUENCE: 56

Gly Ser Thr Ser Gly Ser Gly Lys Pro Gly Ser Gly Glu Gly Ser Thr
1               5                   10                  15

Lys Gly

<210> SEQ ID NO 57
<211> LENGTH: 14
<212> TYPE: PRT
<213> ORGANISM: Artificial
<220> FEATURE:
<223> OTHER INFORMATION: Synthetic construct (linker)

<400> SEQUENCE: 57

Glu Gly Lys Ser Ser Gly Ser Gly Ser Glu Ser Lys Glu Phe
1               5                   10

<210> SEQ ID NO 58

-continued

```
<211> LENGTH: 43
<212> TYPE: PRT
<213> ORGANISM: Artificial
<220> FEATURE:
<223> OTHER INFORMATION: General Formula 1
<220> FEATURE:
<221> NAME/KEY: SITE
<222> LOCATION: (2)..(2)
<223> OTHER INFORMATION: Xaa is aminoisobutyric acid (Aib)
<220> FEATURE:
<221> NAME/KEY: SITE
<222> LOCATION: (13)..(13)
<223> OTHER INFORMATION: Xaa is alanine (Ala, A), Aib, tyrosine (Tyr,
      Y), or glutamine (Gln, Q)
<220> FEATURE:
<221> NAME/KEY: SITE
<222> LOCATION: (14)..(14)
<223> OTHER INFORMATION: Xaa is methionine (Met, M) or leucine (Leu, L)
<220> FEATURE:
<221> NAME/KEY: SITE
<222> LOCATION: (15)..(15)
<223> OTHER INFORMATION: Xaa is aspartic acid (Asp, D) or glutamic acid
      (Glu, E)
<220> FEATURE:
<221> NAME/KEY: SITE
<222> LOCATION: (16)..(16)
<223> OTHER INFORMATION: Xaa is alanine (Ala, A), lysine (Lys, K), or
      glycine (Gly, G)
<220> FEATURE:
<221> NAME/KEY: SITE
<222> LOCATION: (17)..(17)
<223> OTHER INFORMATION: Xaa is isoleucine (Ile, I) or glutamine (Gln,
      Q)
<220> FEATURE:
<221> NAME/KEY: SITE
<222> LOCATION: (19)..(19)
<223> OTHER INFORMATION: Xaa is glutamine (Gln, Q) or alanine (Ala, A)
<220> FEATURE:
<221> NAME/KEY: SITE
<222> LOCATION: (20)..(20)
<223> OTHER INFORMATION: Xaa is glutamine (Gln, Q), Aib, or lysine (Lys,
      K)
<220> FEATURE:
<221> NAME/KEY: SITE
<222> LOCATION: (21)..(21)
<223> OTHER INFORMATION: Xaa is aspartic acid (Asp, D) or glutamic acid
      (Glu, E)
<220> FEATURE:
<221> NAME/KEY: SITE
<222> LOCATION: (23)..(23)
<223> OTHER INFORMATION: Xaa is valine (Val, V) or isoleucine (Ile, I)
<220> FEATURE:
<221> NAME/KEY: SITE
<222> LOCATION: (24)..(24)
<223> OTHER INFORMATION: Xaa is asparagine (Asn, N), alanine (Ala, A),
      or glutamine (Gln, Q)
<220> FEATURE:
<221> NAME/KEY: SITE
<222> LOCATION: (27)..(27)
<223> OTHER INFORMATION: Xaa is leucine (Leu, L) or isoleucine (Ile, I)
<220> FEATURE:
<221> NAME/KEY: SITE
<222> LOCATION: (28)..(28)
<223> OTHER INFORMATION: Xaa is alanine (Ala, A) or Aib
<220> FEATURE:
<221> NAME/KEY: SITE
<222> LOCATION: (29)..(29)
<223> OTHER INFORMATION: Xaa is glutamine (Gln, Q) or glycine (Gly, G)
<220> FEATURE:
<221> NAME/KEY: SITE
<222> LOCATION: (30)..(30)
<223> OTHER INFORMATION: Xaa is lysine (Lys, K), glycine (Gly, G), or
      histidine (His, H)
<220> FEATURE:
<221> NAME/KEY: SITE
<222> LOCATION: (31)..(31)
<223> OTHER INFORMATION: Xaa is proline (Pro, P), glycine (Gly, G), or
      cysteine (Cys, C)
<220> FEATURE:
```

```
<221> NAME/KEY: SITE
<222> LOCATION: (32)..(32)
<223> OTHER INFORMATION: Xaa is serine (Ser, S) or lysine (Lys, K), or
      is absent
<220> FEATURE:
<221> NAME/KEY: SITE
<222> LOCATION: (33)..(33)
<223> OTHER INFORMATION: Xaa is serine (Ser, S) or lysine (Lys, K), or
      is absent
<220> FEATURE:
<221> NAME/KEY: SITE
<222> LOCATION: (34)..(34)
<223> OTHER INFORMATION: Xaa is glycine (Gly, G) or asparagine (Asn, N),
      or is absent
<220> FEATURE:
<221> NAME/KEY: SITE
<222> LOCATION: (35)..(35)
<223> OTHER INFORMATION: Xaa is alanine (Ala, A) or aspartic acid (Asp,
      D), or is absent
<220> FEATURE:
<221> NAME/KEY: SITE
<222> LOCATION: (36)..(36)
<223> OTHER INFORMATION: Xaa is proline (Pro, P) or tryptophan (Trp, W),
      or is absent
<220> FEATURE:
<221> NAME/KEY: SITE
<222> LOCATION: (37)..(37)
<223> OTHER INFORMATION: Xaa is proline (Pro, P) or lysine (Lys, K), or
      is absent
<220> FEATURE:
<221> NAME/KEY: SITE
<222> LOCATION: (38)..(38)
<223> OTHER INFORMATION: Xaa is proline (Pro, P) or histidine (His, H),
      or is absent
<220> FEATURE:
<221> NAME/KEY: SITE
<222> LOCATION: (39)..(39)
<223> OTHER INFORMATION: Xaa is serine (Ser, S), asparagine (Asn, N), or
      cysteine (Cys, C), or is absent
<220> FEATURE:
<221> NAME/KEY: SITE
<222> LOCATION: (40)..(40)
<223> OTHER INFORMATION: Xaa is cysteine (Cys, C) or isoleucine (Ile,
      I), or is absent
<220> FEATURE:
<221> NAME/KEY: SITE
<222> LOCATION: (41)..(41)
<223> OTHER INFORMATION: Xaa is threonine (Thr, T) or is absent
<220> FEATURE:
<221> NAME/KEY: SITE
<222> LOCATION: (42)..(42)
<223> OTHER INFORMATION: Xaa is glutamine (Gln, Q) or is absent
<220> FEATURE:
<221> NAME/KEY: SITE
<222> LOCATION: (43)..(43)
<223> OTHER INFORMATION: Xaa is cysteine (Cys, C) or is absent

<400> SEQUENCE: 58

Tyr Xaa Glu Gly Thr Phe Ile Ser Asp Tyr Ser Ile Xaa Xaa Xaa Xaa
1               5                   10                  15

Xaa Ala Xaa Xaa Xaa Phe Xaa Xaa Trp Leu Xaa Xaa Xaa Xaa Xaa Xaa
            20                  25                  30

Xaa Xaa Xaa Xaa Xaa Xaa Xaa Xaa Xaa Xaa Xaa
        35                  40

<210> SEQ ID NO 59
<211> LENGTH: 43
<212> TYPE: PRT
<213> ORGANISM: Artificial
<220> FEATURE:
<223> OTHER INFORMATION: General Formula 2
<220> FEATURE:
<221> NAME/KEY: SITE
<222> LOCATION: (2)..(2)
<223> OTHER INFORMATION: Xaa is aminoisobutyric acid (Aib)
```

-continued

```
<220> FEATURE:
<221> NAME/KEY: SITE
<222> LOCATION: (13)..(13)
<223> OTHER INFORMATION: Xaa is alanine (Ala, A), Aib, or tyrosine (Tyr,
      Y)
<220> FEATURE:
<221> NAME/KEY: SITE
<222> LOCATION: (14)..(14)
<223> OTHER INFORMATION: Xaa is methionine (Met, M) or leucine (Leu, L)
<220> FEATURE:
<221> NAME/KEY: SITE
<222> LOCATION: (15)..(15)
<223> OTHER INFORMATION: Xaa is aspartic acid (Asp, D) or glutamic acid
      (Glu, E)
<220> FEATURE:
<221> NAME/KEY: SITE
<222> LOCATION: (16)..(16)
<223> OTHER INFORMATION: Xaa is alanine (Ala, A) or lysine (Lys, K)
<220> FEATURE:
<221> NAME/KEY: SITE
<222> LOCATION: (17)..(17)
<223> OTHER INFORMATION: Xaa is isoleucine (Ile, I) or glutamine (Gln,
      Q)
<220> FEATURE:
<221> NAME/KEY: SITE
<222> LOCATION: (19)..(19)
<223> OTHER INFORMATION: Xaa is glutamine (Gln, Q) or alanine (Ala, A)
<220> FEATURE:
<221> NAME/KEY: SITE
<222> LOCATION: (20)..(20)
<223> OTHER INFORMATION: Xaa is glutamine (Gln, Q), Aib, or lysine (Lys,
      K)
<220> FEATURE:
<221> NAME/KEY: SITE
<222> LOCATION: (21)..(21)
<223> OTHER INFORMATION: Xaa is aspartic acid (Asp, D) or glutamic acid
      (Glu, E)
<220> FEATURE:
<221> NAME/KEY: SITE
<222> LOCATION: (24)..(24)
<223> OTHER INFORMATION: Xaa is asparagine (Asn, N) or glutamine (Gln,
      Q)
<220> FEATURE:
<221> NAME/KEY: SITE
<222> LOCATION: (27)..(27)
<223> OTHER INFORMATION: Xaa is leucine (Leu, L) or isoleucine (Ile, I)
<220> FEATURE:
<221> NAME/KEY: SITE
<222> LOCATION: (28)..(28)
<223> OTHER INFORMATION: Xaa is alanine (Ala, A) or Aib
<220> FEATURE:
<221> NAME/KEY: SITE
<222> LOCATION: (29)..(29)
<223> OTHER INFORMATION: Xaa is glutamine (Gln, Q) or glycine (Gly, G)
<220> FEATURE:
<221> NAME/KEY: SITE
<222> LOCATION: (30)..(30)
<223> OTHER INFORMATION: Xaa is lysine (Lys, K), glycine (Gly, G), or
      histidine (His, H)
<220> FEATURE:
<221> NAME/KEY: SITE
<222> LOCATION: (31)..(31)
<223> OTHER INFORMATION: Xaa is proline (Pro, P) or glycine (Gly, G)
<220> FEATURE:
<221> NAME/KEY: SITE
<222> LOCATION: (32)..(32)
<223> OTHER INFORMATION: Xaa is serine (Ser, S) or lysine (Lys, K)
<220> FEATURE:
<221> NAME/KEY: SITE
<222> LOCATION: (33)..(33)
<223> OTHER INFORMATION: Xaa is serine (Ser, S) or lysine (Lys, K)
<220> FEATURE:
<221> NAME/KEY: SITE
<222> LOCATION: (34)..(34)
<223> OTHER INFORMATION: Xaa is glycine (Gly, G) or asparagine (Asn, N)
<220> FEATURE:
<221> NAME/KEY: SITE
<222> LOCATION: (35)..(35)
<223> OTHER INFORMATION: Xaa is alanine (Ala, A) or aspartic acid (Asp,
```

-continued

```
                  D)
<220> FEATURE:
<221> NAME/KEY: SITE
<222> LOCATION: (36)..(36)
<223> OTHER INFORMATION: Xaa is proline (Pro, P) or tryptophan (Trp, W)
<220> FEATURE:
<221> NAME/KEY: SITE
<222> LOCATION: (37)..(37)
<223> OTHER INFORMATION: Xaa is proline (Pro, P) or lysine (Lys, K)
<220> FEATURE:
<221> NAME/KEY: SITE
<222> LOCATION: (38)..(38)
<223> OTHER INFORMATION: Xaa is proline (Pro, P) or histidine (His, H)
<220> FEATURE:
<221> NAME/KEY: SITE
<222> LOCATION: (39)..(39)
<223> OTHER INFORMATION: Xaa is serine (Ser, S), asparagine (Asn, N), or
      cysteine (Cys, C)
<220> FEATURE:
<221> NAME/KEY: SITE
<222> LOCATION: (40)..(40)
<223> OTHER INFORMATION: Xaa is cysteine (Cys, C) or isoleucine (Ile,
      I), or is absent
<220> FEATURE:
<221> NAME/KEY: SITE
<222> LOCATION: (41)..(41)
<223> OTHER INFORMATION: Xaa is threonine (Thr, T) or is absent
<220> FEATURE:
<221> NAME/KEY: SITE
<222> LOCATION: (42)..(42)
<223> OTHER INFORMATION: Xaa is glutamine (Gln, Q) or is absent
<220> FEATURE:
<221> NAME/KEY: SITE
<222> LOCATION: (43)..(43)
<223> OTHER INFORMATION: Xaa is cysteine (Cys, C) or is absent

<400> SEQUENCE: 59

Tyr Xaa Glu Gly Thr Phe Ile Ser Asp Tyr Ser Ile Xaa Xaa Xaa Xaa
1               5                   10                  15

Xaa Ala Xaa Xaa Xaa Phe Val Xaa Trp Leu Xaa Xaa Xaa Xaa Xaa Xaa
            20                  25                  30

Xaa Xaa Xaa Xaa Xaa Xaa Xaa Xaa Xaa Xaa Xaa
        35                  40

<210> SEQ ID NO 60
<211> LENGTH: 43
<212> TYPE: PRT
<213> ORGANISM: Artificial
<220> FEATURE:
<223> OTHER INFORMATION: General Formula 3
<220> FEATURE:
<221> NAME/KEY: SITE
<222> LOCATION: (2)..(2)
<223> OTHER INFORMATION: Xaa is aminoisobutyric acid (Aib)
<220> FEATURE:
<221> NAME/KEY: SITE
<222> LOCATION: (13)..(13)
<223> OTHER INFORMATION: Xaa is alanine (Ala, A) or Aib
<220> FEATURE:
<221> NAME/KEY: SITE
<222> LOCATION: (14)..(14)
<223> OTHER INFORMATION: Xaa is methionine (Met, M) or leucine (Leu, L)
<220> FEATURE:
<221> NAME/KEY: SITE
<222> LOCATION: (15)..(15)
<223> OTHER INFORMATION: Xaa is aspartic acid (Asp, D) or glutamic acid
      (Glu, E)
<220> FEATURE:
<221> NAME/KEY: SITE
<222> LOCATION: (16)..(16)
<223> OTHER INFORMATION: Xaa is alanine (Ala, A) or lysine (Lys, K)
<220> FEATURE:
<221> NAME/KEY: SITE
<222> LOCATION: (17)..(17)
<223> OTHER INFORMATION: Xaa is isoleucine (Ile, I) or glutamine (Gln,
```

```
      Q)
<220> FEATURE:
<221> NAME/KEY: SITE
<222> LOCATION: (19)..(19)
<223> OTHER INFORMATION: Xaa is glutamine (Gln, Q) or alanine (Ala, A)
<220> FEATURE:
<221> NAME/KEY: SITE
<222> LOCATION: (20)..(20)
<223> OTHER INFORMATION: Xaa is glutamine (Gln, Q) or Aib
<220> FEATURE:
<221> NAME/KEY: SITE
<222> LOCATION: (21)..(21)
<223> OTHER INFORMATION: Xaa is aspartic acid (Asp, D) or glutamic acid
      (Glu, E)
<220> FEATURE:
<221> NAME/KEY: SITE
<222> LOCATION: (28)..(28)
<223> OTHER INFORMATION: Xaa is alanine (Ala, A) or Aib
<220> FEATURE:
<221> NAME/KEY: SITE
<222> LOCATION: (29)..(29)
<223> OTHER INFORMATION: Xaa is glutamine (Gln, Q) or glycine (Gly, G)
<220> FEATURE:
<221> NAME/KEY: SITE
<222> LOCATION: (30)..(30)
<223> OTHER INFORMATION: Xaa is lysine (Lys, K), glycine (Gly, G), or
      histidine (His, H)
<220> FEATURE:
<221> NAME/KEY: SITE
<222> LOCATION: (31)..(31)
<223> OTHER INFORMATION: Xaa is proline (Pro, P) or glycine (Gly, G)
<220> FEATURE:
<221> NAME/KEY: SITE
<222> LOCATION: (32)..(32)
<223> OTHER INFORMATION: Xaa is serine (Ser, S) or lysine (Lys, K)
<220> FEATURE:
<221> NAME/KEY: SITE
<222> LOCATION: (33)..(33)
<223> OTHER INFORMATION: Xaa is serine (Ser, S) or lysine (Lys, K)
<220> FEATURE:
<221> NAME/KEY: SITE
<222> LOCATION: (34)..(34)
<223> OTHER INFORMATION: Xaa is glycine (Gly, G) or asparagine (Asn, N)
<220> FEATURE:
<221> NAME/KEY: SITE
<222> LOCATION: (35)..(35)
<223> OTHER INFORMATION: Xaa is alanine (Ala, A) or aspartic acid (Asp,
      D)
<220> FEATURE:
<221> NAME/KEY: SITE
<222> LOCATION: (36)..(36)
<223> OTHER INFORMATION: Xaa is proline (Pro, P) or tryptophan (Trp, W)
<220> FEATURE:
<221> NAME/KEY: SITE
<222> LOCATION: (37)..(37)
<223> OTHER INFORMATION: Xaa is proline (Pro, P) or lysine (Lys, K)
<220> FEATURE:
<221> NAME/KEY: SITE
<222> LOCATION: (38)..(38)
<223> OTHER INFORMATION: Xaa is proline (Pro, P) or histidine (His, H)
<220> FEATURE:
<221> NAME/KEY: SITE
<222> LOCATION: (39)..(39)
<223> OTHER INFORMATION: Xaa is serine (Ser, S) or asparagine (Asn, N)
<220> FEATURE:
<221> NAME/KEY: SITE
<222> LOCATION: (40)..(40)
<223> OTHER INFORMATION: Xaa is cysteine (Cys, C) or isoleucine (Ile, I)
<220> FEATURE:
<221> NAME/KEY: SITE
<222> LOCATION: (41)..(41)
<223> OTHER INFORMATION: Xaa is threonine (Thr, T) or is absent
<220> FEATURE:
<221> NAME/KEY: SITE
<222> LOCATION: (42)..(42)
<223> OTHER INFORMATION: Xaa is glutamine (Gln, Q) or is absent
<220> FEATURE:
<221> NAME/KEY: SITE
<222> LOCATION: (43)..(43)
```

-continued

```
<223> OTHER INFORMATION: Xaa is cysteine (Cys, C) or is absent

<400> SEQUENCE: 60

Tyr Xaa Glu Gly Thr Phe Ile Ser Asp Tyr Ser Ile Xaa Xaa Xaa Xaa
1               5                   10                  15

Xaa Ala Xaa Xaa Xaa Phe Val Asn Trp Leu Leu Xaa Xaa Xaa Xaa Xaa
            20                  25                  30

Xaa Xaa Xaa Xaa Xaa Xaa Xaa Xaa Xaa Xaa Xaa
        35                  40
```